(12) United States Patent
Leber et al.

(10) Patent No.: US 10,703,800 B2
(45) Date of Patent: Jul. 7, 2020

(54) CELL CULTURE MEDIUM

(71) Applicant: La Jolla Biologics, Inc., San Diego, CA (US)

(72) Inventors: Christopher T. Leber, San Diego, CA (US); Michael W.Y. Shen, San Diego, CA (US); Yiwen Tao, San Diego, CA (US); Hugh Eugene Murray, IV, San Diego, CA (US)

(73) Assignee: LA JOLLA BIOLOGICS, INC., San Diego, CA (US)

( * ) Notice: Subject to any disclaimer, the term of this patent is extended or adjusted under 35 U.S.C. 154(b) by 339 days.

(21) Appl. No.: 15/498,221

(22) Filed: Apr. 26, 2017

(65) Prior Publication Data
US 2017/0305999 A1 Oct. 26, 2017

Related U.S. Application Data

(60) Provisional application No. 62/327,964, filed on Apr. 26, 2016.

(51) Int. Cl.
C07K 16/00 (2006.01)
C12N 5/00 (2006.01)
C12P 21/00 (2006.01)

(52) U.S. Cl.
CPC ............ *C07K 16/00* (2013.01); *C12N 5/0018* (2013.01); *C12P 21/005* (2013.01);
(Continued)

(58) Field of Classification Search
None
See application file for complete search history.

(56) References Cited

U.S. PATENT DOCUMENTS 5,378,612 A 1/1995 Nakashima et al.
RE39,792 E * 8/2007 Keen .................. C07K 16/2893
435/325
2015/0175956 A1 6/2015 Elhofy et al.

FOREIGN PATENT DOCUMENTS

KR 102015012578 A 11/2015
WO WO-2015/157335 A1 10/2015
WO WO-2017/189679 A1 11/2017

OTHER PUBLICATIONS

Ishii et al., J. Biosci. Bioeng. 119(4): 478-485 (2015; published online Nov. 7, 2014).*

(Continued)

*Primary Examiner* — Erin M. Bowers
(74) *Attorney, Agent, or Firm* — Mintz Levin Cohn Ferris Glovsky and Popeo PC; Terri Shieh-Newton; David Dang

(57) ABSTRACT

Provided herein, inter alia, are compositions and methods for culturing mammalian cells. In certain aspects, the composition is a medium containing one or more of a lithium ion source, one or more fatty acids, and/or ethanol. Use of any of the cell culture media described herein to culture cells that have been genetically engineered to produce one or more recombinant polypeptides (for example, antibodies) can result in increased titers, a more favorable glycosylation profile, and/or modulated (e.g. decreased) amounts of high and low molecular weight species, and/or modulated (e.g. decreased) amounts of acidic or basic charge variants, compared to cells cultured in a medium that does not contain one or more of a lithium ion source, one or more fatty acids, and/or ethanol.

25 Claims, 20 Drawing Sheets

(52) U.S. Cl.
CPC ...... *C07K 2317/14* (2013.01); *C07K 2317/41* (2013.01); *C07K 2317/73* (2013.01); *C12N 2500/12* (2013.01); *C12N 2500/30* (2013.01); *C12N 2500/36* (2013.01); *C12N 2510/02* (2013.01)

(56) References Cited

OTHER PUBLICATIONS

Ha et al., Appl. Microbiol. Biotechnol. 98: 9239-9248 (2014).*
International Preliminary Report on Patentability issued for International Patent Application No. PCT/US2017/029566, dated Oct. 30, 2018 (Oct. 30, 2018), 6 pages.
International Search Report issued for International Patent Application No. PCT/US2017/029566 dated Aug. 1, 2017, 3 pages.
Supplementary European Search Report issued in European Application No. 17790317.6, dated Oct. 11, 2019 (Oct. 11, 2019), 14 pages.
Written Opinion issued for International Patent Application No. PCT/US2017/029566 dated Aug. 1, 2017, 5 pages.

Goetze, A. et al., (Jul. 2011). "High-mannose glycans on the Fc Region of therapeutic IgG antibodies increase serum clearance in humans," Glycobiology, 21(7):949-959.
Kanda, Y. et al., (2006). "Comparison of biological activity among nonfucosylated therapeutic IgG1 antibodies with three different N-linked Fc oligosaccharides: the high-mannose, hybrid, and complex types", Glycobiology, 17(1):104-118.
Kaufman, R.J. (1990). "Vectors Used for Expression in Mammalian Cells," Methods in Enzymology, 185:487-511.
Li, F. et al., (2010). "Cell culture processes for monoclonal antibody production," mAbs, 2(5):466-477.
Liu, L., (Jun. 2015). "Antibody Glycosylation and Its Impact on the Pharmacokinetics and Pharmacodynamics of Monoclonal Antibodies and Fc-Fusion Proteins," Journal of Pharmaceutical Sciences, 104(6):1866-1884.
Ha, T.K. et al. (Aug. 2014). "Effect of lithium chloride on the production and sialylation of Fc-fusion protein in Chinese hamster ovary cell culture," Applied Microbiology and Biotechnology, 98(22):9239-9248.
Tao, Y., et al., (Apr. 2012). "Novel cholesterol feeding strategy enables a high-density cultivation of cholesterol-dependent NS0 cells in linear low-density polyethylene-based disposable bioreactors", Biotechnology Lett, 34(8):1453-1458.

* cited by examiner

CELL CULTURE MEDIUM

CROSS-REFERENCE TO RELATED APPLICATIONS

This application claims priority to U.S. Provisional Patent Application No. 62/327,964, filed Apr. 26, 2016, the disclosure of which is incorporated by reference herein in its entirety.

FIELD OF INVENTION

The invention relates generally to the field of cell culture media and methods for using the same to produce useful cultured cell-derived products.

BACKGROUND

Commercial production of cell culture-derived products (for example, protein-based products, such as monoclonal antibodies (mAbs)), requires optimization of cell culture parameters in order for the cells to produce enough product to meet clinical and commercial demands. However, when cell culture parameters are optimized for improving productivity of a protein product, it is also necessary to maintain desired quality specifications of the product such as glycosylation profile, aggregate levels, charge heterogeneity, and amino acid sequence integrity (Li, et al., 2010, *mAbs.*, 2(5):466-477).

For instance, an increase of over 20% volumetric titer results in a significant improvement in large-scale monoclonal antibody production economics. Additionally, the ability to control the glycan forms of proteins produced in cell culture is important. Glycan species have been shown to significantly influence pharmacokinetics (PK) and pharmacodynamics (PD) of therapeutic proteins such as mAbs. Moreover, the ability to modulate the relative percentage of various glycan species can have drastic results over the behavior of a protein in vivo. For example, increased mannose-5-N-acetylglycosamine-2 ("Man5") and other high-mannose glycan species have been shown to decrease mAb in vivo half-life (Liu, 2015, *J Pharm Sci.*, 104(6):1866-84; Goetze et al., 2011, *Glycobiology*, 21(7):949-59; and Kanda et al. 2007, *Glycobiology*, 17(1):104-18). On the other hand, glycosylated mAbs with mannose-3-N-acetylglycosamine-4 ("G0") glycan species have been shown to impact antibody dependent cellular cytotoxicity (ADCC).

Bioreactors have been successfully utilized for the cell-based production of therapeutic proteins using fed-batch, immobilized, perfusion and continuous modes. Strategies, such as the use of temperature, media formulation, including the addition of growth inhibitors, autocrine factors or cyclic mononucleotides, and hyperstimulation by osmolarity stress, have been used to enhance protein production by cells in culture. To the extent that they have worked at all, these approaches have shown only marginal success.

As such, there is a particular need for improved compositions for use in cell culture for the production of medically or industrially useful products, such as antibodies. Ideally, such compositions and methods for utilizing the same would result in higher titers, modulated (e.g. decreased) high and low molecular weight species, as well as a more favorable glycosylation profile of the derived products in cell culture.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

The invention provided herein discloses, inter alia, compositions and methods for culturing mammalian cells. In certain aspects, the composition is a medium containing one or more of a lithium ion source, one or more fatty acids, and/or ethanol. Use of any of the cell culture media described herein to culture cells that have been genetically engineered to produce one or more recombinant polypeptides (for example, antibodies) can result in increased titers, a modulated glycosylation profile, modulated amounts of acidic or basic charge species, and/or modulated amounts of high and low molecular weight species compared to using media that do not contain one or more of a lithium ion source, one or more fatty acids, and/or ethanol.

Accordingly, in some aspects, provided herein is a medium for culturing mammalian cells comprising: (a) (i) a basal medium or (ii) a feed medium; and (b) one or more sources of lithium ions. In some embodiments, the cells have been genetically engineered to produce one or more recombinant polypeptides. In some embodiments of any of the embodiments disclosed herein, the medium further comprises (c) ethanol; and/or (d) one or more fatty acids. In some embodiments, said one or more fatty acids is selected from the group consisting of oleic acid, linoleic acid, linolenic acid, myristic acid, palmitic acid and stearic acid. In some embodiments of any of the embodiments disclosed herein, said one or more sources of lithium ions is selected from the group of one or more of lithium acetate, lithium chloride, lithium carbonate, lithium oxybutyrate, lithium orotate, lithium bromide, lithium citrate, lithium fluoride, lithium iodide, lithium nitrate, and lithium sulfate. In some embodiments of any of the embodiments disclosed herein, said lithium ions are present in a concentration from about 0.1 µM to about 25 mM. In some embodiments of any of the embodiments disclosed herein, the titer of said one or more recombinant polypeptides is increased compared to the titer of recombinant polypeptides produced by mammalian cells that are not cultured in said medium. In some embodiments of any of the embodiments disclosed herein, the amount of high molecular weight species of said one or more recombinant polypeptides produced by said cells is modulated (e.g. decreased) compared to recombinant polypeptides produced by mammalian cells that are not cultured in said medium. In some embodiments of any of the embodiments disclosed herein, the amount of low molecular weight species of said one or more recombinant polypeptides produced by said cells is modulated (e.g. decreased) compared to recombinant polypeptides produced by mammalian cells that are not cultured in said medium. In some embodiments of any of the embodiments disclosed herein, the glycosylation profile (e.g., the amount of glycosylation) of said one or more recombinant polypeptides produced by said cells is modulated compared to recombinant polypeptides produced by mammalian cells that are not cultured in said medium. In some embodiments, said modulated glycosylation comprises modulated (e.g., decreased) terminal mannose glycan species. In some embodiments, said modulated glycosylation comprises modulation of one or more glycan species selected from mannose-5-N-acetylglycosamine-2 (Man5), mannose-6-N-acetylglycosamine-2 (Man6), mannose-3-N-acetylglucosamine-4 (G0), mannose-3-N-acetylglucosamine-4-fucose (G0F), mannose-3-N-acetylglucosamine-4-galactose-1-fucose (G1F), or mannose-3-N- acetylglucosamine-4-galactose-2-fucose (G2F). In some embodiments of any of the embodiments disclosed herein, the amount of acidic or basic charge variants of said one or more recombinant polypeptides produced by said cells is modulated (e.g., decreased) compared to recombinant polypeptides produced by mammalian cells that are not cultured in said medium. In some embodiments of any of the embodiments disclosed herein, ethanol is present at a concentration from about 0.001% to about 4% (v/v). In some embodiments of any of the embodiments disclosed herein, the one or more fatty acids are present at a concentration (such as a daily feeding concentration) of about 1 µM to about 4 mM (such as any of about 1 M, 10 M, 25 M, 50 M, 75 M, 100 M, 200 M, 300 M, 400 M, 500 M, 600 M, 700 M, 800 M, 900 M, 1 mM, 1.5 mM, 2 mM, 2.5 mM, 3 mM, 3.5 mM, or 4 mM, inclusive of all values falling in between these numbers).

In other aspects, provided herein is a medium for culturing mammalian cells comprising: (a) (i) a basal medium or (ii) a feed medium; and (b) ethanol. In some embodiments, the cells have been genetically engineered to produce one or more recombinant polypeptides. In some embodiments of any of the embodiments disclosed herein, the medium further comprises (c) one or more fatty acids. In some embodiments, said one or more fatty acids is selected from Butyric (C4), Valeric (C5), Caproic (C6), Enanthic (C7), Caprylic (C8), Pelargonic (C9), Capric (C10), Undecylic (C11), Lauric (C12), Tridecylic (C13), Myristic (C14), Pentadecanoic (C15), Palmitic (C16), Margaric (C17), Stearic (C18), Nonadecylic (C19), Arachidic (C20), Heneicosylic (C21), Behenic (C22), Tricosylic (C23), Lignoceric (C24), Pentacosylic (C25), Cerotic (C26), Heptacosylic (C27), Montanic (C28), Nonacosylic (C29), Melissic (C30), Hentriacontylic (C31), Lacceroic (C32), Psyllic (C33), Geddic (C34), Ceroplastic (C35), Hexatriacontylic (C36), Heptatriacontanoic (C37), or Octatriacontanoic (C38) acids. In some embodiments of any of the embodiments disclosed herein, ethanol is present at a concentration from about 0.001% to about 4% (v/v). In some embodiments of any of the embodiments disclosed herein, the titer of said one or more recombinant polypeptides is increased compared to the titer of recombinant polypeptides produced by mammalian cells that are not cultured in said medium. In some embodiments of any of the embodiments disclosed herein, the amount of high molecular weight species of said one or more recombinant polypeptides produced by said cells is modulated (e.g. decreased) compared to recombinant polypeptides produced by mammalian cells that are not cultured in said medium. In some embodiments of any of the embodiments disclosed herein, the amount of low molecular weight species of said one or more recombinant polypeptides produced by said cells is modulated (e.g. decreased) compared to recombinant polypeptides produced by mammalian cells that are not cultured in said medium. In some embodiments of any of the embodiments disclosed herein, the glycosylation profile (e.g., the amount of glycosylation) of said one or more recombinant polypeptides produced by said cells is modulated compared to recombinant polypeptides produced by mammalian cells that are not cultured in said medium. In some embodiments, said modulated glycosylation comprises modulated (e.g., decreased) terminal mannose glycan species. In some embodiments, modulated glycosylation comprises modulation of one or more glycan species selected from mannose-5-N-acetylglycosamine-2 (Man5), mannose-6-N-acetylglycosamine-2 (Man6), mannose-3-N-acetylglucosamine-4 (G0), mannose-3-N-acetylglucosamine-4-fucose (G0F), mannose-3-N-acetylglucosamine-4-galactose-1-fucose (G1F), or mannose-3-N-acetylglucosamine-4-galactose-2-fucose (G2F). In some embodiments of any of the embodiments disclosed herein, the amount of acidic or basic charge variants of said one or more recombinant polypeptides produced by said cells is modulated (e.g., decreased) compared to recombinant polypeptides produced by mammalian cells that are not cultured in said medium. In some embodiments of any of the embodiments disclosed herein, the one or more fatty acids are present at a concentration (such as a daily feeding concentration) of about 1 M to about 4 mM (such as any of about 1 M, 10 M, 25 M, 50 M, 75 M, 100 M, 200 M, 300 M, 400 M, 500 M, 600 M, 700 M, 800 M, 900 M, 1 mM, 1.5 mM, 2 mM, 2.5 mM, 3 mM, 3.5 mM, or 4 mM, inclusive of all values falling in between these numbers).

In further aspects, provided herein is a medium for culturing mammalian cells comprising: (a) (i) a basal medium or (ii) a feed medium; and (b) one or more fatty acids. In some embodiments, the cells have been genetically engineered to produce one or more recombinant polypeptides. In some embodiments of any of the embodiments disclosed herein, the one or more fatty acids are present at a daily feeding concentration of about 1 µM-1 mM. In some embodiments of any of the embodiments disclosed herein, the amount of high molecular weight species of said one or more recombinant polypeptides produced by said cells is modulated (e.g. decreased) compared to recombinant polypeptides produced by mammalian cells that are not cultured in said medium. In some embodiments of any of the embodiments disclosed herein, the amount of low molecular weight species of said one or more recombinant polypeptides produced by said cells is modulated (e.g. decreased) compared to recombinant polypeptides produced by mammalian cells that are not cultured in said medium. In some embodiments of any of the embodiments disclosed herein, the glycosylation profile (e.g., the amount of glycosylation) of said one or more recombinant polypeptides produced by said cells is modulated compared to recombinant polypeptides produced by mammalian cells that are not cultured in said medium. In some embodiments, said modulated glycosylation comprises modulated (e.g., decreased) terminal mannose glycan species. In some embodiments, modulated glycosylation comprises modulation of one or more glycan species selected from mannose-5-N-acetylglycosamine-2 (Man5), mannose-3-N-acetylglucosamine-4 (G0), mannose-3-N-acetylglucosamine-4-galactose-1-fucose (G1F), or mannose-3-N-acetylglucosamine-4-galactose-2-fucose (G2F). In some embodiments of any of the embodiments disclosed herein, the amount of acidic or basic charge variants of said one or more recombinant polypeptides produced by said cells is modulated (e.g., decreased) compared to recombinant polypeptides produced by mammalian cells that are not cultured in said medium. In some embodiments of any of the embodiments disclosed herein, the glycosylation profile of said one or more recombinant polypeptides is modulated (e.g., altered) compared to mammalian cells that are not cultured in said medium. In some embodiments of any of the embodiments disclosed herein, the fatty acid is one or more of thymol, cholesteryl acetate, methyl octanoate, 1-octanoyl-rac-glycerol, oleic acid, linoleic acid, linolenic acid, cholesterol, palmitic acid, stearic acid, and/or myristic acid.

In yet other aspects, provided herein is a method for producing one or more recombinant polypeptides from an engineered mammalian cell, the method comprising: (a) culturing said engineered mammalian cell in any of the cell culture media disclosed herein under suitable conditions for the production of said one or more recombinant polypeptides; and (b) producing said one or more recombinant polypeptides. In some embodiments, the method further comprises (c) isolating said one or more recombinant polypeptides. In some embodiments of any of the embodiments disclosed herein, the medium is a basal medium. In some embodiments of any of the embodiments disclosed herein, the medium is a feed medium. In some embodiments of any of the embodiments disclosed herein, said one or more recombinant polypeptides is an antibody or fragment thereof. In some embodiments, said antibody is a monoclonal antibody. In some embodiments, the monoclonal antibody inhibits the growth of a proliferating cell. In some embodiments, said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), integrin $\alpha_v\beta_3$, neural apoptosis-regulated proteinase 1, integrin $\alpha_{IIb}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7. In some embodiments, said monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

In another aspect, provided herein are methods for modulating the glycosylation profile of one or more recombinant polypeptides produced by a genetically engineered mammalian cell, the method comprising: (a) culturing said mammalian cell in any of the cell culture media disclosed herein under suitable conditions for the production of said one or more recombinant polypeptides; and (b) producing said one or more recombinant polypeptides, wherein said one or more recombinant polypeptides has a modulated glycosylation profile compared to recombinant polypeptides produced by mammalian cells that are not cultured in any of the cell culture media disclosed herein. In some embodiments, said modulated glycosylation profile comprises modulated (e.g., decreased) terminal mannose glycan species. In some embodiments, said modulated glycosylation comprises modulation of one or more glycan species selected from mannose-5-N-acetylglycosamine-2 (Man5), mannose-6-N-acetylglycosamine-2 (Man6), mannose-3-N-acetylglucosamine-4 (G0), mannose-3-N-acetylglucosamine-4-fucose (G0F), mannose-3-N-acetylglucosamine-4-galactose-1-fucose (G1F), and/or mannose-3-N-acetylglucosamine-4-galactose-2-fucose (G2F). In some embodiments of any of the embodiments disclosed herein, the ratio of the terminal mannose glycan species to the total sum of glycan species is modulated (e.g., decreased) by about 40% to about 50%. In some embodiments of any of the embodiments disclosed herein, said one or more recombinant polypeptides is an antibody or fragment thereof. In some embodiments, said antibody is a monoclonal antibody. In some embodiments, the monoclonal antibody inhibits the growth of a proliferating cell. In some embodiments, said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), integrin $\alpha_v\beta_3$, neural apoptosis-regulated proteinase 1, integrin $\alpha_{IIb}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7. In some embodiments, the monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

In another aspect, provided herein are methods for modulating (e.g., reducing) the amount of high or low molecular weight species of one or more recombinant polypeptides produced by an engineered mammalian cell, the method comprising: (a) culturing said mammalian cell in any of the cell culture media disclosed herein under suitable conditions for the production of said one or more recombinant polypeptides; and (b) producing said one or more recombinant polypeptides, wherein said one or more recombinant polypeptides have reduced amounts of high or low molecular weight species compared to recombinant polypeptides produced by mammalian cells that are not cultured in any of the cell culture media disclosed herein. In some embodiments, said one or more recombinant polypeptides has reduced amounts of high molecular weight species. In some embodiments, said one or more recombinant polypeptides have reduced amounts of low molecular weight species. In some embodiments, said low molecular weight species comprise polypeptide fragments that are not completely assembled and/or folded. In some embodiments, said high molecular weight species comprise more than one subunit of a recombinant polypeptide. In some embodiments of any of the embodiments disclosed herein, the percent specific ratio of low molecular weight species to the sum of all (1) non-aggregated; (2) low molecular weight species; and (3) high molecular weight species is modulated (e.g. decreased) relative to the percent specific ratio compared to recombinant polypeptides produced by mammalian cells that are not cultured in any of the cell culture media disclosed herein. In some embodiments of any of the embodiments disclosed herein, the percent specific ratio of high molecular weight species to the sum of all (1) non-aggregated; (2) low molecular weight species; and (3) high molecular weight species is modulated (e.g. decreased) relative to the percent specific ratio compared to recombinant polypeptides produced by mammalian cells that are not cultured in any of the cell culture media disclosed herein. In some embodiments of any of the embodiments disclosed herein, said one or more recombinant polypeptides is an antibody or fragment thereof. In some embodiments, said antibody is a monoclonal antibody. In some embodiments, the monoclonal antibody inhibits the growth of a proliferating cell. In some embodiments, said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), integrin $\alpha_v\beta_3$, neural apoptosis-regulated proteinase 1, integrin $\alpha_{IIb}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7. In some embodiments, said monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

In further aspects, provided herein are methods for modulating (e.g. reducing) the amount of acidic or basic charge species of one or more recombinant polypeptides produced by an engineered mammalian cell, the method comprising: (a) culturing said mammalian cell in any of the cell culture media disclosed herein under suitable conditions for the production of said one or more recombinant polypeptides; and (b) producing said one or more recombinant polypeptides, wherein said one or more recombinant polypeptides have reduced amounts of acidic charge species compared to recombinant polypeptides produced by mammalian cells that are not cultured in any of the cell culture media disclosed herein. In some embodiments, the percent specific ratio of acidic or basic charge species to the total sum of all (1) acidic species; (2) main species; and (3) basic charge species is reduced relative to recombinant polypeptides produced by mammalian cells that are not cultured in any of the cell culture media disclosed herein. In some embodiments of any of the embodiments disclosed herein, said one or more recombinant polypeptides is an antibody or fragment thereof. In some embodiments of any of the embodiments disclosed herein, said antibody is a monoclonal antibody. In some embodiments, said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), integrin $\alpha_v\beta_3$, neural apoptosis-regulated proteinase 1, integrin $\alpha_{IIb}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7. In some embodiments of any of the embodiments disclosed herein, said monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab. In some embodiments of any of the embodiments disclosed herein, the medium is a basal medium. In some embodiments of any of the embodiments disclosed herein, the medium is a feed medium.

In another aspect, provided herein is a kit comprising: (a) (i) a mammalian cell culture basal medium and/or (ii) a mammalian cell culture feed medium; and (b) one or more sources of lithium ions. In some embodiments of any of the embodiments disclosed herein, said kit further comprises (c) ethanol and/or (d) one or more fatty acids. In some embodiments, said one or more fatty acids is selected from Butyric (C4), Valeric (C5), Caproic (C6), Enanthic (C7), Caprylic (C8), Pelargonic (C9), Capric (C10), Undecylic (C11), Lauric (C12), Tridecylic (C13), Myristic (C14), Pentadecanoic (C15), Palmitic (C16), Margaric (C17), Stearic (C18), Nonadecylic (C19), Arachidic (C20), Heneicosylic (C21), Behenic (C22), Tricosylic (C23), Lignoceric (C24), Pentacosylic (C25), Cerotic (C26), Heptacosylic (C27), Montanic (C28), Nonacosylic (C29), Melissic (C30), Hentriacontylic (C31), Lacceroic (C32), Psyllic (C33), Geddic (C34), Ceroplastic (C35), Hexatriacontylic (C36), Heptatriacontanoic (C37), or Octatriacontanoic (C38) acids. In some embodiments of any of the embodiments disclosed herein, said kit further comprises (e) written instructions for culturing mammalian cells. In some embodiments of any of the embodiments disclosed herein, said one or more sources of lithium ions is selected from the group of one or more of lithium acetate, lithium chloride, lithium carbonate, lithium oxybutyrate, lithium orotate, lithium bromide, lithium citrate, lithium fluoride, lithium iodide, lithium nitrate, and lithium sulfate.

In other aspects, provided herein are recombinant polypeptides produced by culturing an engineered mammalian cell in any of the cell culture media disclosed herein under suitable conditions for the production of said recombinant polypeptide. In some embodiments, said polypeptide is an antibody or fragment thereof. In some embodiments of any of the embodiments disclosed herein, said antibody is a monoclonal antibody. In some embodiments, the monoclonal antibody inhibits the growth of a proliferating cell. In some embodiments, said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of B. anthracis, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (ox-LDL), platelet-derived growth factor receptor beta, neuropilin 1, Von Willebrand factor (vWF), integrin $\alpha_v\beta_3$, neural apoptosis-regulated proteinase 1, integrin $\alpha_{IIb}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7. In some embodiments, said monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

Each of the aspects and embodiments described herein are capable of being used together, unless excluded either explicitly or clearly from the context of the embodiment or aspect.

DETAILED DESCRIPTION

Figure 1:
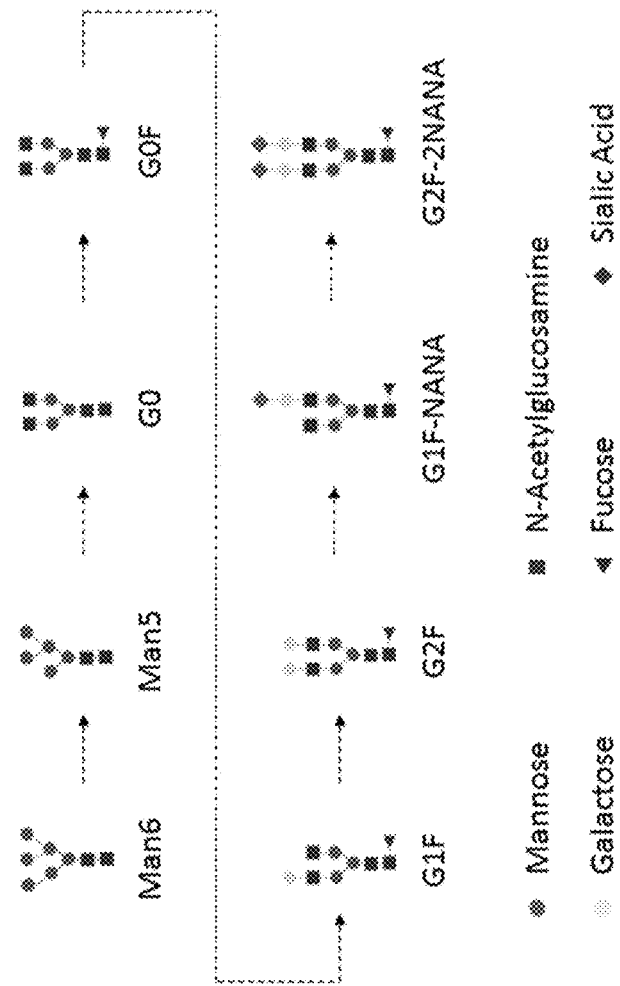
FIG. 1 depicts a schematic representation of major N-glycan linked species following the typical maturation pathway. Glycosylation processing begins in the Endoplasmic Reticulum with further processing in the cis-, medial- and trans-Golgi. Major glycan species shown, include: mannose-6-N-acetylglycosamine-2 (Man6), mannose-5-N-acetylglycosamine-2 (Man5), mannose-3-N-acetylglucosamine-4 (G0), mannose-3-N-acetylglucosamine-4-fucose (G0F), mannose-3-N-acetylglucosamine-4-galactose-1-fucose (G1F), mannose-3-N-acetylglucosamine-4-galactose-2-fucose (G2F), mannose-3-N-acetylglucosamine-4-galactose-1-fucose-1-N-acetylneuraminic-1 (G1F-NANA) and mannose-3-N-acetylglucosamine-4-galactose-2-fucose-1-N-acetylneuraminic-2 (G2F-2NANA).

This invention provides, inter alia, methods, compositions, and kits for the culturing of mammalian cells. The invention is based, in part, on the inventors' discovery that culturing mammalian cells genetically engineered to produce one or more recombinant polypeptides in a medium containing one or more of a lithium ion source, ethanol, and/or one or more fatty acids resulted in increased polypeptide titer as well as reduced high and low molecular weight species. Additionally, use of the compositions described herein resulted in polypeptide products having a more favorable glycosylation profile compared to mammalian cells that are not cultured in the media described herein. Consequently, use of the cell culture media compositions disclosed herein can not only increase the amount of product produced by engineered mammalian cells, thereby resulting in more favorable production economics, but can also result in products with glycosylation profiles that impart added benefits for in vivo administration of those products, such as improved pharmacokinetics (PK) and/or pharmacodynamics (PD).

I. General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons, Inc., New York, 2000, (including supplements through 2014), *Gene Transfer and Expression in Mammalian Cells* (Makrides, ed., Elsevier Sciences B.V., Amsterdam, 2003), and *Current Protocols in Immunology* (Horgan K and S. Shaw (1994) (including supplements through 2014).

II. Definitions

A "basal medium," as used herein, is a medium used for culturing eukaryotic cells which is, itself, directly used to culture the cells and is not used as an additive to other media, although various components may be added to a basal medium. For example, if CHO cells were cultured in DMEM, a well-known, commercially-available medium for mammalian cells, and periodically fed with glucose or other nutrients, DMEM would be considered the basal medium. Other examples of basal media include, without limitation, MEM medium, IMDM medium, 199/109 medium, HamF10/F12 medium, McCoy's 5A medium, and RPMI 1640 medium.

A "feed medium" is a medium used as a feed in a culture of eukaryotic cells, which may be, for example, mammalian cells. A feed medium, like a basal medium, is designed with regard to the needs of the particular cells being cultured. Thus, a basal medium can be used as a basis for designing a feed medium. As described below in more detail, a feed medium can have higher concentrations of most, but not all, components of a base culture medium. For example, some components, such as, for example, nutrients including amino acids or carbohydrates, may be at about 2×, 3×, 4×, 5×, 6×, 7×, 8×, 9×, 10×, 12×, 14×, 16×, 20×, 30×, 50×, 100×, 200×, 400×, 600×, 800×, or even about 1000× of their normal concentrations in a basal medium. Other components, such as salts, maybe kept at about 1× of the basal medium concentration, as one would want to keep the feed isotonic with the basal medium. Thus, in some embodiments, various components are added to keep the feed medium physiologic and others are added because they replenish nutrients to the cell culture.

A "recombinant polypeptide" or a "recombinant protein" is a protein resulting from the process of genetic engineering. Cells are "genetically engineered" when recombinant nucleic acid sequences that allow expression of the recombinant protein have been introduced into the cells such as viral infection with a recombinant virus, transfection, transformation, or electroporation. See e.g. Kaufman et al. (1990), *Meth. Enzymol.* 185: 487-511; *Current Protocols in Molecular Biology*, Ausubel et al., eds. (Wiley & Sons, New York, 1988, and quarterly updates through 2015). In some embodiments, a recombinant polypeptide is an antibody or functional fragment thereof.

The term "genetic engineering" refers to a recombinant DNA or RNA method used to create a host cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired protein. The methods of "genetic engineering" also encompass numerous methods including, but not limited to, amplifying nucleic acids using polymerase chain reaction, assembling recombinant DNA molecules by cloning them in *Escherichia coli*, restriction enzyme digestion of nucleic acids, ligation of nucleic acids, and transfer of bases to the ends of nucleic acids, among numerous other methods that are well-known in the art. See e.g. Sambrook et al., *Molecular Cloning: A Laboratory Manual*, 2nd ed., vol. 1-3, Cold Spring Harbor Laboratory, 1989, as well as updates through the present The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

III. Compositions of the Invention

In some aspect, provided herein is a medium for culturing mammalian cells containing a basal medium or a feed medium as well as one or more of (1) a source of lithium ions, (2) ethanol, and/or (3) one or more fatty acids.

A. Mammalian Cells

Any mammalian cell capable of being cultured is suitable for use in the present invention. This includes cells derived from humans (for example, HeLa cells) as well as cells derived from rodents such as mice, rats, hamsters (for example Chinese hamster ovary (CHO) cells), or Guinea pigs. It also includes mammalian cells derived from other species, particularly primate species.

Examples of mammalian cells that can be cultured in the media according to the present invention include, without limitation, murine C127 cells, 3T3 cells, COS cells, human osteosarcoma cells, MRC-5 cells, baby hamster kidney (BHK) cells, VERO cells, HEK 293 cells, rHEK 293 cells, normal human fibroblast cells, Stroma cells, Hepatocytes cells, or PER.C6 cells. Examples of hybridomas that may be cultured in the process according to the present invention include, e.g., DA4.4 calls, 123A cells, 127A cells, GAMMA cells and 67-9-B cells.

Further examples of mammalian cells appropriate for use with the compositions disclosed herein are COP cells, L cells, C 127 cells, Sp2/0 cells, NS-O cells, NS-I cells, NIH3T3 cells, PC12 cells, PC12 h cells, COS1 cells, COS3 cells, COS7 cells, CV1 cells, Chinese hamster ovary (CHO) cells, African green monkey kidney (AGMK) cells, or a cell derived from diploid fibroblasts, from cancer cells (such as myeloma cells), and HepG2 cells.

B. Cells Genetically Engineered to Produce Recombinant Polypeptides

In another aspect, the mammalian cells cultured in any of the media described herein can be genetically engineered to produce one or more recombinant polypeptides. For purposes of the present invention, mammalian cells can be genetically engineered in accordance with any method known in the art. For example, expression vectors can be designed to contain nucleic acid sequences which optimize gene expression for certain host mammalian cell strains. Such optimization components include, but are not limited to origin of replication, promoters, and enhancers. The vectors and components referenced herein are described for exemplary purposes and are not meant to narrow the scope of the invention. Suitable vectors are those which are compatible with the mammalian host cell employed. Suitable vectors can be derived, for example, from a bacterium, a virus (such as bacteriophage T7 or an M-13 derived phage), a cosmid, a yeast, or a plant. Suitable vectors can be maintained in low, medium, or high copy number in the mammalian host cell. Protocols for obtaining and using such vectors are known to those in the art (see, for example, Sambrook et al., *Molecular Cloning: A Laboratory Manual*, 4th ed., Cold Spring Harbor, 2012).

A nucleic acid sequence encoding a desired polypeptide or an expression vector comprising the same can be inserted into a mammalian cell (e.g., a CHO cell or any other mammalian cell described herein) using standard techniques for introduction of a DNA construct or vector into a mammalian host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., *Molecular Cloning: A Laboratory Manual*, 4th ed., Cold Spring Harbor, 2012). The introduced nucleic acids may be integrated into chromosomal DNA or maintained as extrachromosomal replicating sequences. Transformants can be selected by any method known in the art.

C. Sources of Lithium Ions

In some aspects of any of the mammalian cell culture media described herein, the medium contains one or more sources of lithium ions. Any lithium ion source is suitable for use in the present invention and includes lithium salts, solvates, and metal.

Nonlimiting sources of lithium ions include lithium hydroxide (LiOH and LiOH.H$_2$O), lithium carbonate (Li$_2$CO$_3$), lithium methoxide, lithium acetate, lithium oxide (Li$_2$O) lithium peroxide (Li$_2$O$_2$), lithium hydride (LiH), lithium chloride (LiCl), lithium fluoride (LiF), lithium iodide (LiI), lithium sulfide (Li$_2$S), lithium sulfite (LiSO$_3$), lithium sulfate (LiSO$_4$), lithium superoxide (LiO$_2$), lithium carbide (Li$_2$C$_2$), lithium tetrachloroaluminate (LiAlCl$_4$), lithium aluminum hydride (LiAlH$_4$), lithium aluminium oxide (LiAlO$_2$), lithium tetrafluoroborate (LiBF$_4$), lithium borohydride (LiBH$_4$), lithium metaborate (LiBO$_2$), lithium tetraborate (Li$_2$B$_4$O$_7$), lithium triborate (LiB$_3$O$_5$), lithium hypochlorite (LiClO), lithium chlorate (LiClO$_3$), lithium perchlorate (LiClO$_4$), lithium cobalt oxide (LiCoO$_2$), lithium iodate (LiIO$_3$), lithium amide (LiNH$_2$), lithium imide (Li$_2$NH), liithium azide (LiN$_3$), lithium nitrite (LiNO$_2$), lithium nitrate (LiNO$_3$), lithium tetraborate (Li$_2$B$_4$O$_7$), lithium carbide (Li$_2$C2), and lithium molybdate (Li$_2$MoO$_4$).

In some embodiments, the amount of the lithium ion source present in the medium (for example, a basal medium or a feed medium) can range from about 0.05 mM to about 15 mM, such as any of about 0.05 mM to about 0.5 mM, about 0.1 mM to about 0.75 mM, about 0.25 mM to about 1 mM, about 0.5 mM to about 1.25 mM, about 0.75 mM to about 1.5 mM, about 1 mM to about 1.75 mM, about 1.25 mM to about 1.75 mM, about 1.25 mM to about 2.25 mM, about 1.5 mM to about 2.5 mM, about 1.75 mM to about 2.75 mM, about 2 mM to about 3 mM, about 2.5 mM to about 3.5 mM, about 3 mM to about 4 mM, about 3.5 mM to about 4.5 mM, about 4 mM to about 5 mM, about 4.5 mM to about 5.5 mM, about 5 mM to about 6 mM, about 5.5 mM to about 6.5 mM, about 6 mM to about 7 mM, about 6.5 mM to about 8.5 mM, about 7.5 mM to about 9.5 mM, about 8.5 mM to about 11.5 mM, about 9.5 mM to about 12.5 mM, about 11.5 mM to about 13.5 mM, about 12.5 mM to about 15 mM, about 14 mM to about 17 mM, about 16 mM to about 19 mM, about 18 mM to about 21 mM, about 20 mM to about 23 mM, about 22 mM to about 25 mM, about 0.75 mM to about 1.75 mM, about 0.5 mM to about 10 mM, about 0.5 mM to about 7.5 mM, about 1 mM to about 5 mM, about 1 mM to about 4 mM, about 1 mM to about 3 mM, about 1 mM to about 2 mM, or about 1 mM to about 1.25 mM.

In other embodiments, the amount of the lithium ion source present in the medium (for example, a basal medium or a feed medium) is any of about 0.05 mM, 0.1 mM, 0.15 mM, 0.2 mM, 0.25 mM, 0.3 mM, 0.35 mM, 0.4 mM, 0.45 mM, 0.5 mM, 0.55 mM, 0.6 mM, 0.65 mM, 0.7 mM, 0.75 mM, 0.8 mM, 0.85 mM, 0.9 mM, 0.95 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.1 mM, 3.2 mM, 3.3 mM, 3.4 mM, 3.5 mM, 3.6 mM, 3.7 mM, 3.8 mM, 3.9 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.1 mM, 5.2 mM, 5.3 mM, 5.4 mM, 5.5 mM, 5.6 mM, 5.7 mM, 5.8 mM, 5.9 mM, 6 mM, 6.1 mM, 6.2 mM, 6.3 mM, 6.4 mM, 6.5 mM, 6.6 mM, 6.7 mM, 6.8 mM, 6.9 mM, 7 mM, 7.1 mM, 7.2 mM, 7.3 mM, 7.4 mM, 7.5 mM, 7.6 mM, 7.7 mM, 7.8 mM, 7.9 mM, 8 mM, 8.1 mM, 8.2 mM, 8.3 mM, 8.4 mM, 8.5 mM, 8.6 mM, 8.7 mM, 8.8 mM, 8.9 mM, 9 mM, 9.1 mM, 9.2 mM, 9.3 mM, 9.4 mM, 9.5 mM, 9.6 mM, 9.7 mM, 9.8 mM, 9.9 mM, 10 mM, 10.1 mM, 10.2 mM, 10.3 mM, 10.4 mM, 10.5 mM, 10.6 mM, 10.7 mM, 10.8 mM, 10.9 mM, 11 mM, 11.1 mM, 11.2 mM, 11.3 mM, 11.4 mM, 11.5 mM, 11.6 mM, 11.7 mM, 11.8 mM, 11.9 mM, 12 mM, 12.1 mM, 12.2 mM, 12.3 mM, 12.4 mM, 12.5 mM, 12.6 mM, 12.7 mM, 12.8 mM, 12.9 mM, 13 mM, 13.1 mM, 13.2 mM, 13.3 mM, 13.4 mM, 13.5 mM, 13.6 mM, 13.7 mM, 13.8 mM, 13.9 mM, 14 mM, 14.1 mM, 14.2 mM, 14.3 mM, 14.4 mM, 14.5 mM, 14.6 mM, 14.7 mM, 14.8 mM, 14.9 mM, 15 mM, 16 mM, 17 mM, 18 mM, 19 mM, 20 mM, 21 mM, 22 mM, 23 mM, 24 mM, 25 mM, or more, inclusive of all values falling in between these numbers.

D. Fatty Acids

In some aspects of any of the mammalian cell culture media described herein, the medium contains one or more fatty acids. Any fatty acid is suitable for use in the present invention. As used herein, "fatty acid" refers to any member of the family of naturally occurring or synthetically produced hydrocarbons containing a carboxylic acid, and at least one saturated, unsaturated, partially unsaturated, or conjugated carbon-carbon bond. Furthermore, the term fatty acid is used generally to describe fatty acids, C2-C38 fatty acids, conjugated fatty acids, lipids, phospholipids, oils, fats, triacylglycerides, fatty acid derivatives, diacyl glycerol, isoprenoids, sphingolipids, glycerolipids, and the like.

In some embodiments, the fatty acid is a saturated fatty acid such as, without limitation, one or more of Butyric (C4), Valeric (C5), Caproic (C6), Enanthic (C7), Caprylic (C8), Pelargonic (C9), Capric (C10), Undecylic (C11), Lauric (C12), Tridecylic (C13), Myristic (C14), Pentadecanoic (C15), Palmitic (C16), Margaric (C17), Stearic (C18), Nonadecylic (C19), Arachidic (C20), Heneicosylic (C21), Behenic (C22), Tricosylic (C23), Lignoceric (C24), Pentacosylic (C25), Cerotic (C26), Heptacosylic (C27), Montanic (C28), Nonacosylic (C29), Melissic (C30), Hentriacontylic (C31), Lacceroic (C32), Psyllic (C33), Geddic (C34), Ceroplastic (C35), Hexatriacontylic (C36), Heptatriacontanoic (C37), or Octatriacontanoic (C38) acids.

In other embodiments, the fatty acid is an omega-3 (ω-3) unsaturated fatty acid such as, without limitation, one or more of α-Linolenic (18:3), Stearidonic (18:4), Eicosapentaenoic (20:5), or Docosahexaenoic (22:6) acids.

In additional embodiments, the fatty acid is an omega-6 (ω-6) unsaturated fatty acid such as, without limitation, one or more of Linoleic (18:2), γ-Linolenic (18:3), Dihomo-γ-linolenic (20:3), Arachidonic (20:4), or Adrenic (22:4) acids.

In yet other embodiments, the fatty acid is an omega-7 (ω-7) unsaturated fatty acid such as, without limitation, one or more of Palmitoleic (16:1), Vaccenic (18:1), or Paullinic (20:1) acids.

In another embodiment, the fatty acid is an omega-9 (ω-9) unsaturated fatty acid such as, without limitation, one or more of Oleic (18:1), Elaidic (trans-18:1), Gondoic (20:1), Erucic (22:1), Nervonic (24:1), or Mead (20:3) acid.

As used herein, the term "isoprenoid" refers to a large and diverse class of naturally-occurring class of organic compounds composed of two or more units of hydrocarbons, with each unit consisting of five carbon atoms arranged in a specific pattern. As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

In some embodiments, the amount of fatty acids present in the medium (for example, a basal medium or a feed medium) can range from about 1 µM to about 1 mM, such as any of about 1 µM to about 5 µM, about 1 µM to about 10 µM, about 1 µM to about 15 µM, about 1 µM to about 20 µM, about 1 µM to about 25 µM, about 1 µM to about 30 µM, about 1 µM to about 35 µM, about 1 µM to about 40 µM, about 1 µM to about 45 µM, about 1 µM to about 50 µM, about 1 µM to about 55 µM, about 1 µM to about 60 µM, about 1 µM to about 65 µM, about 1 µM to about 70 µM, about 1 µM to about 75 µM, about 1 µM to about 80 µM, about 10 µM to about 20 µM, about 10 µM to about 30 µM, about 10 µM to about 40 µM, about 10 µM to about 50 µM, about 10 µM to about 60 µM, about 10 µM to about 70 µM, about 10 µM to about 80 µM, about 10 µM to about 90 µM, about 20 µM to about 40 µM, about 20 µM to about 60 µM, about 20 µM to about 80 µM, about 20 µM to about 100 µM, about 30 µM to about 50 µM, about 30 µM to about 60 µM, about 30 µM to about 70 µM, about 30 µM to about 80 µM, about 30 µM to about 90 µM, about 40 µM to about 50 µM, about 40 µM to about 60 µM, about 40 µM to about 80 µM, about 40 µM to about 90 µM, about 50 µM to about 60 µM, about 50 µM to about 70 µM, about 50 µM to about 80 µM, about 50 µM to about 90 µM, about 50 µM to about 100 µM, about 60 µM to about 70 µM, about 60 µM to about 80 µM, about 60 µM to about 90 µM, about 60 µM to about 100 µM, about 70 µM to about 80 µM, about 70 µM to about 90 µM, about 70 µM to about 100 µM, about 50 µM to about 150 µM, about 100 µM to about 200 µM, about 150 µM to about 250 µM, about 200 µM to about 300 µM, about 250 µM to about 350 µM, about 300 µM to about 400 µM, about 350 µM to about 450 µM, about 400 µM to about 500 µM, about 450 µM to about 550 µM, about 500 µM to about 600 µM, about 550 µM to about 650 µM, about 600 µM to about 700 µM, about 650 µM to about 750 µM, about 700 µM to about 800 µM, about 750 µM to about 850 µM, about 800 µM to about 900 µM, about 850 µM to about 950 µM, about or 900 µM to about 1 mM.

In other embodiments, the amount of the fatty acids present in the medium (for example, a basal medium or a feed medium) is any of about 1 µM, 2 µM, 3 µM, 4 µM, 5 µM, 6 µM, 7 µM, 8 µM, 9 µM, 10 µM, 11 µM, 12 µM, 13 M, 14 M, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 51 µM, 52 µM, 53 µM, 54 µM, 55 µM, 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82 µM, 83 µM, 84 µM, 85 µM, 86 µM, 87 µM, 88 µM, 89 µM, 90 µM, 91 µM, 92 µM, 93 µM, 94 µM, 95 µM, 96 µM, 97 µM, 98 µM, 99 µM, 100 µM, 125 µM, 150 µM, 175 µM, 200 µM, 225 µM, 250 µM, 275 µM, 300 µM, 325 µM, 350 M, 375 µM, 400 µM, 425 µM, 450 µM, 475 µM, 500 µM, 525 µM, 550 µM, 575 µM, 600 µM, 625 µM, 650 µM, 675 µM, 700 µM, 725 µM, 750 µM, 775 µM, 800 µM, 825 µM, 850 µM, 875 µM, 900 µM, 925 µM, 950 µM, 975 µM, or 1 mM, inclusive of all numbers falling in between these values.

In some embodiments, the fatty acid is one or more of thymol, cholesteryl acetate, methyl octanoate, 1-octanoyl-rac-glycerol, oleic acid, linoleic acid, linolenic acid, cholesterol, palmitic acid, stearic acid, and myristic acid.

In one embodiment, cell culture media supplementation with one or more of thymol, 1-octanoyl-rac-glycerol, linoleic acid, and/or linolenic acid increases the titer of recombinant protein produced by cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the titer of the recombinant protein produced in media not supplemented with one or more of the fatty acids.

In some embodiments, the phrase "modulating" or "modulates" with respect to the relative percentage of 1) a HMW and/or LMW species; or 2) an acidic and/or basic charge species refers to increasing the relative percentage of 1) a particular HMW and/or LMW species; or 2) a particular acidic and/or basic charge species of a recombinant polypeptide. However, in other embodiments, the phrase "modulating" or "modulates" with respect to the relative percentage of 1) a HMW and/or LMW species; or 2) an acidic and/or basic charge species refers to decreasing the relative percentage of 1) a particular HMW and/or LMW species; or 2) a particular acidic and/or basic charge species of a recombinant polypeptide.

In another embodiment, cell culture media supplementation with one or more of thymol, cholesterol acetate, methyl octanoate, 1-octanoyl-rac-glycerol, palmitic acid, stearic acid, and myristic acid modulates the relative percentage of HMW species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of HMW species of the recombinant protein produced in media not supplemented with one or more of the fatty acids.

In a further embodiment, cell culture media supplementation with one or more of thymol, cholesteryl acetate, 1-octanoyl-rac-glycerol, linoleic acid, linolenic acid, palmitic acid, and stearic acid modulates the relative percentage of LMW species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of LMW species of the recombinant protein produced in media not supplemented with one or more of the fatty acids.

In yet other embodiments, cell culture media supplementation with one or more of thymol, cholesteryl acetate, methyl octanoate, 1-octanoyl-rac-glycerol, oleic acid, linoleic acid, linolenic acid, palmitic acid, and myristic acid modulates the relative percentage of acidic charge species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of acidic charge species of the recombinant protein produced in media not supplemented with one or more of the fatty acids.

In additional embodiments, cell culture media supplementation with one or more of thymol, cholesteryl acetate, methyl octanoate, 1-octanoyl-rac-glycerol, cholesterol, palmitic acid, stearic acid, and myristic acid modulates the relative percentage of basic charge species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of basic charge species of the recombinant protein produced in media not supplemented with one or more of the fatty acids.

In another embodiment, cell culture media supplementation with one or more of thymol, cholesteryl acetate, methyl octanoate, 1-octanoyl-rac-glycerol, oleic acid, linoleic acid, linolenic acid, cholesterol, palmitic acid, stearic acid, and myristic acid modulates (for example, increases or decreases) the relative percentage of Man5% glycan species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of Man5% glycan species of the recombinant protein produced in media not supplemented with one or more of the fatty acids.

In still further embodiments, cell culture media supplementation with one or more of thymol, cholesteryl acetate, methyl octanoate, oleic acid, linoleic acid, linolenic acid, cholesterol, palmitic acid, stearic acid, and myristic acid modulates (for example, increases or decreases) the relative percentage of G0% glycan species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of G0% glycan species of the recombinant protein produced in media not supplemented with one or more of the fatty acids.

In additional embodiments, cell culture media supplementation with one or more of cholesteryl acetate, methyl octanoate, 1-octanoyl-rac-glycerol, oleic acid, and myristic acid modulates (for example, increases or decreases) the relative percentage of G0F % glycan species produced by recombinant protein-producing cell lines grown in the media by any of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 60%, 70%, 80%, 90%, or 100%, inclusive of percentages falling in between these values, relative to the amount of G0F % glycan species of the recombinant protein produced in media not supplemented with one or more of the fatty acids.

E. Ethanol

In further aspects of any of the mammalian cell culture media described herein, the medium contains ethanol.

In some embodiments, the amount of ethanol present in the medium (for example, a basal medium or a feed medium) can range from about 0.001% to about 4% (v/v), such as any of about 0.001% to about 0.01% (v/v), about 0.001% to about 0.02% (v/v), about 0.001% to about 0.05% (v/v), about 0.001% to about 0.075% (v/v), about 0.001% to about 0.09% (v/v), about 0.001% to about 0.1% (v/v), about 0.001% to about 0.15% (v/v), about 0.001% to about 0.2% (v/v), about 0.001% to about 0.25% (v/v), about 0.001% to about 0.3% (v/v), about 0.05% to about 0.075% (v/v), about 0.05% to about 0.1% (v/v), about 0.05% to about 0.15% (v/v), about 0.05% to about 0.2% (v/v), about 0.05% to about 0.25% (v/v), about 0.05% to about 0.3% (v/v), about 0.1% to about 0.15% (v/v), about 0.1% to about 0.2% (v/v), about 0.1% to about 0.25% (v/v), about 0.1% to about 0.3% (v/v), about 0.1% to about 0.4% (v/v), about 0.1% to about 0.5% (v/v), about 0.25% to about 0.5% (v/v), about 0.5% to about 1.5% (v/v), about 0.75% to about 1.75% (v/v), about 1% to about 2% (v/v), about 1.25% to about 2.25% (v/v), about 1.5% to about 2.5% (v/v), about 1.75% to about 2.75% (v/v), about 2% to about 3% (v/v), about 2.25% to about 3.25% (v/v), about 2.5% to about 3.5% (v/v), about 2.75% to about 3.75% (v/v), about 3% to about 4% (v/v).

In other embodiments, the amount of ethanol present in the medium (for example, a basal medium or a feed medium) can be any of about 0.001% (v/v), 0.005% (v/v), 0.01% (v/v), 0.011% (v/v), 0.012% (v/v), 0.013% (v/v), 0.014% (v/v), 0.015% (v/v), 0.016% (v/v), 0.017% (v/v), 0.018% (v/v), 0.019% (v/v), 0.02% (v/v), 0.021% (v/v), 0.022% (v/v), 0.023% (v/v), 0.024% (v/v), 0.025% (v/v), 0.026% (v/v), 0.027% (v/v), 0.028% (v/v), 0.029% (v/v), 0.03% (v/v), 0.031% (v/v), 0.032% (v/v), 0.033% (v/v), 0.034% (v/v), 0.035% (v/v), 0.036% (v/v), 0.037% (v/v), 0.038% (v/v), 0.039% (v/v), 0.04% (v/v), 0.041% (v/v), 0.042% (v/v), 0.043% (v/v), 0.044% (v/v), 0.045% (v/v), 0.046% (v/v), 0.047% (v/v), 0.048% (v/v), 0.049% (v/v), 0.05% (v/v), 0.051% (v/v), 0.052% (v/v), 0.053% (v/v), 0.054% (v/v), 0.055% (v/v), 0.056% (v/v), 0.057% (v/v), 0.058% (v/v), 0.059% (v/v), 0.06% (v/v), 0.061% (v/v), 0.062% (v/v), 0.063% (v/v), 0.064% (v/v), 0.065% (v/v), 0.066% (v/v), 0.067% (v/v), 0.068% (v/v), 0.069% (v/v), 0.07, % (v/v) 0.071, % (v/v) 0.072, % (v/v) 0.073% (v/v), 0.074% (v/v), 0.075% (v/v), 0.076% (v/v), 0.077% (v/v), 0.078% (v/v), 0.079% (v/v), 0.08% (v/v), 0.081% (v/v), 0.082% (v/v), 0.083% (v/v), 0.084% (v/v), 0.085% (v/v), 0.086% (v/v), 0.087% (v/v), 0.088% (v/v), 0.089% (v/v), 0.09% (v/v), 0.091% (v/v), 0.092% (v/v), 0.093% (v/v), 0.094% (v/v), 0.095% (v/v), 0.096% (v/v), 0.097% (v/v), 0.098% (v/v), 0.099% (v/v), 0.1% (v/v), 0.11% (v/v), 0.12% (v/v), 0.13% (v/v), 0.14% (v/v), 0.15% (v/v), 0.16% (v/v), 0.17% (v/v), 0.18% (v/v), 0.19% (v/v), 0.2% (v/v), 0.21% (v/v), 0.22% (v/v), 0.23% (v/v), 0.24% (v/v), 0.25% (v/v), 0.26% (v/v), 0.27% (v/v), 0.28% (v/v), 0.29% (v/v), 0.3% (v/v), 0.31% (v/v), 0.32% (v/v), 0.33% (v/v), 0.34% (v/v), 0.35% (v/v), 0.36% (v/v), 0.37% (v/v), 0.38% (v/v), 0.39% (v/v), 0.4% (v/v), 0.41% (v/v), 0.42% (v/v), 0.43% (v/v), 0.44% (v/v), 0.45% (v/v), 0.46% (v/v), 0.47% (v/v), 0.48% (v/v), 0.49% (v/v), 0.5% (v/v), 0.6% (v/v), 0.7% (v/v), 0.8% (v/v), 0.9% (v/v), 1% (v/v), 1.1% (v/v), 1.2% (v/v), 1.3% (v/v), 1.4% (v/v), 1.5% (v/v), 1.6% (v/v), 1.7% (v/v), 1.8% (v/v), 1.9% (v/v), 2% (v/v), 2.1% (v/v), 2.2% (v/v), 2.3% (v/v), 2.4% (v/v), 2.5% (v/v), 2.6% (v/v), 2.7% (v/v), 2.8% (v/v), 2.9% (v/v), 3% (v/v), 3.1% (v/v), 3.2% (v/v), 3.3% (v/v), 3.4% (v/v), 3.5% (v/v), 3.6% (v/v), 3.7% (v/v), 3.8% (v/v), 3.9% (v/v), or 4% (v/v) or more, inclusive of all values falling in between these percentages.

IV. Methods of the Invention

A. Methods for Producing Recombinant Polypeptides

In some aspects, provided herein are methods for producing one or more recombinant polypeptides from an engineered mammalian cell. The method entails culturing the engineered mammalian cell in any of the mammalian cell culture medium compositions described herein under suitable conditions for the production of one or more recombinant polypeptides; and producing one or more recombinant polypeptides.

Culturing of recombinant mammalian cells for the production of recombinant polypeptides is well known in the art. The polypeptides that can be produced from the cell culture media according to the present invention are not limited. The term "polypeptide" as used herein encompasses molecules composed of a chain of more than two amino acids joined by peptide bonds; molecules containing two or more such chains; molecules comprising one or more such chains being additionally modified, e.g., by glycosylation. The term polypeptide is intended to encompass proteins.

Any polypeptide that can be expressed in a mammalian host cell may be produced according to the present invention. After the polypeptide(s) has/have been produced in the media of the present invention it is either extracellularly secreted, bound to the cells or remains in the cells, depending on the specific product and cell line used. The polypeptide product can be recovered from culture supernatant directly or after lysis of the cells by standard procedures. In further embodiments, isolation and purification of recombinant polypeptides is performed using standard techniques known in the art. These can include, without limitation, size exclusion chromatography, protein A affinity chromatography, anion exchange chromatography, cation exchange chromatography, mixed mode chromatography, or hydrophobic interaction chromatography.

One non-limiting class of polypeptides produced by the cell culture media according to the present invention is recombinant antibodies. The term "antibody" is used in the broadest sense and specifically covers monoclonal antibodies (including full length monoclonal antibodies), polyclonal antibodies, multi-specific antibodies (e.g., bispecific antibodies), nanobodies modified antibodies, subunits of antibodies, antibody derivatives, artificial antibodies, combinations of antibodies with proteins and antibody fragments sufficiently long to display the desired biological activity. The monoclonal antibodies as used herein may be human antibodies or humanized antibodies. In one embodiment, the recombinant polypeptide is a monoclonal antibody selected from the group consisting of trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

However, polypeptides other than antibodies can also be produced using cell cultures and the cell culture media according to the present invention, e.g. therapeutic polypeptides such as, without limitation, transmembrane proteins, receptors, hormones, growth factors, proteases, clotting and anti-clotting proteins, inhibitor proteins, interleukins, transport factors, fusion proteins and the like. As such, another non-limiting class of polypeptides produced in the cell culture media according to the present invention is therapeutic polypeptides. In one embodiment, the recombinant polypeptide is a therapeutic polypeptide selected from the group consisting of abatacept, abobotulinumtoxinA, aflibercept, agalsidase beta, albiglutide, aldesleukin, alglucosidase alfa, alteplase, cathflo activase, anakinra, asfotase alfa, asparaginase, becaplermin, belatacept, collagenase, collagenase clostridium histolyticum, darbepoetin alfa, denileukin, diftitox, dornase alfa, dulaglutide, ecallantide, elosulfase alfa, epoetin alfa, etanercept, filgrastim, galsulfase, glucarpidase, idursulfase, incobotulinumtoxinA, interferon alfa-2b, interferon alfa-n3, interferon beta-1a, interferon beta-1a, interferon beta-1b, interferon beta-1b, interferon gamma-1b, laronidase, methoxy polyethylene glycol-epoetin beta, metreleptin, ocriplasmin, onabotulinumtoxinA, oprelvekin, palifermin, parathyroid hormone, pegaspargase, pegfilgrastim, peginterferon alfa-2a, peginterferon alfa-2a, ribavirin, peginterferon alfa-2b, peginterferon beta-1a, pegloticase, rasburicase, reteplase, rilonacept, rimabotulinumtoxinB, romiplostim, sargramostim, sebelipase, tbo-filgrastim, tenecteplase, and ziv-aflibercept.

In some embodiments, it may be advantageous to change the temperature during the course of culturing the mammalian cells and include one or more temperature shifts that are initiated at certain time points. A change/shift in the temperature does not refer to spontaneous fluctuations in the temperature, but to changes in temperature of at least 1° C. or alternatively at least 2° C., 3° C., 4° C., 5° C., 6° C., 7° C., 8° C., 9° C., or 10° C. that are intended, and where the second temperature is being maintained for at least one day. A change/shift can be implemented by altering the temperature set point of the culture. The timing is dependent on either the growth state of the culture, a predetermined number of days after the start of the culture or the metabolic needs of the cells. Thus, the temperature may be shifted in a period of about 1 to 10 days after starting the culture. In some embodiments, a temperature shift is done during the growth phase of the cells or towards the end of this phase and prior to the beginning of the production phase of the recombinant protein. Depending on the culture vessel volume, the change may occur rapidly or more slowly and lasts several hours, in one example such a shift in temperature is implemented during the growth phase of the culture when the density is between about 40 and about 90% of the maximal density. In one example the first temperature is between about 33 and about 38° C., while in other examples the first temperature is between about 35 and about 37° C. The second temperature is between about 28 and about 36° C., or alternatively between about 29 and about 35° C.

In another embodiment of the present invention, it may be advantageous to change the pH during the course of the culturing of the mammalian cells by including one or more pH shifts. In further aspects of the invention shifts in temperature may also be combined with one or more shifts in the pH. In other embodiments, the pH of the culture medium (such as any mammalian cell culture media described herein) can vary during the course of fermentation, such as from between about pH 6.7 to about pH 7.3, such as any pH of about 6.7, 6.8, 6.9, 7.0, 7.1, 7.2, or 7.3.

The cell culture medium according to the present invention can be used in various mammalian cell culture processes. Cultivation of cells can be carried out in adherent culture, for instance in monolayer culture or in suspension culture. Large scale cultivation of cells can be used for instance by the various fermentation processes established in industrial biotechnology using, for example, small or large scale bioreactors. Continuous and discontinuous cell culture processes can be utilized using the cell culture media according to the present invention. Other known reactor technologies, e.g. perfusion technologies or the like can be also utilized.

Batch processes are also a possible embodiment. Batch cell culture includes fed-batch culture or simple batch culture. The term "fed-batch cell culture" refers to cell culture wherein mammalian cells and cell culture medium are supplied to the culturing vessel initially and additional culture nutrients are fed continuously or in discrete increments to the culture during the culturing process with or without periodic cell and/or product harvest before termination of the culture. The term "simple batch culture" relates to a procedure in which all components for cell culturing including the mammalian cells and the cell culture medium are supplied to the culturing vessel at the start of the culturing process.

According to one embodiment of the present invention feeding of the cultures is done in a fed-batch process. Such feeding is beneficial for the cells to replace media components and nutrients that are depleted in the media during the culture process. Typically feed solutions comprise amino acids, at least one carbohydrate as an energy source, trace elements, vitamins or specific ions. The feed solutions are added depending on the needs of the cells, which are either based on a predetermined schedule that has been determined for the particular cell line or cell clone and product or measured during the culture process. It is particularly advantageous to use concentrated feed solutions in order to avoid large volume increase and dilution of the media. In some embodiments it may also be useful to have at least two different feed solutions. This allows independent dosing of two or more different groups of nutrients and components to the cells and thus a better adjustment of the feeding conditions concerning optimal supply of certain nutrients.

The products obtained from such cell culture processes can be used for the preparation of pharmaceutical compositions. The term "pharmaceutical composition" indicates a composition suitable or adapted for administration to a mammal, for example, a human. In addition, the protein(s) according to the invention can be administered together with other components of biologically active agents such as pharmaceutically acceptable surfactants, recipients, carriers, diluents and vehicles. In further embodiments, recombinant polypeptides produced in accordance with any of the methods of the present invention can be lyophilized and formulated for intravenous, parenteral, or subcutaneous administration.

In some embodiments, culturing of mammalian cells in any of the media disclosed herein in accordance with any of the methods disclosed herein results in an increased recombinant protein titer in comparison to production by mammalian cells that are not cultured in any of the media disclosed herein in accordance with any of the methods disclosed herein. In some embodiments, the method increases the titer of the recombinant polypeptide by any of about 1% to about 2%, about 1% to about 3%, about 1% to about 4%, about 1% to about 5%, about 2.5% to about 5%, about 2.5% to about 7.5%, about 5% to about 7.5%, about 5% to about 10%, about 1 to about 15%, about 7.5% to about 12.5%, about 7.5% to about 15%, about 7.5% to about 17.5%, about 10% to about 12.5%, about 10% to about 15%, about 10% to about 17.5%, about 10% to about 20%, about 12.5% to about 15%, about 12.5% to about 17.5%, about 12.5% to about 20%, about 12.5% to about 22.5%, about 15% to about 17.5%, about 15% to about 20%, about 15% to about 22.5%, about 15% to about 25%, about 17.5% to about 20%, about 17.5% to about 22.5%, about 17.5% to about 25%, about 17.5% to about 27.5%, about 20% to about 22.5%, about 20% to about 25%, about 20% to about 27.5%, about 20% to about 30%, about 22.5% to about 25%, about 22.5% to about 27.5%, about 22.5% to about 30%, about 22.5% to about 32.5%, about 25% to about 27.5%, about 25% to about 30%, about 25% to about 32.5%, or about 25% to about 35%, or at least any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%, inclusive of values falling in between these percentages, compared to the titer of recombinant polypeptides produced by mammalian cells that are not cultured in the media disclosed herein and in accordance with the methods described herein.

B. Methods for Modulating the Glycosylation Profile of Recombinant Polypeptides

Glycan species have been shown to significantly influence pharmacokinetics (PK) and pharmacodynamics (PD) of therapeutic proteins such as mAbs. Accordingly, in other aspects of the present invention, provided herein are methods for modulating the glycosylation profile of one or more recombinant polypeptides produced by a genetically engineered mammalian cell. In some embodiments, the method involves culturing a mammalian cell in any of the cell culture media described herein (such as a lithium-containing, an ethanol-containing, and/or a fatty acid-containing cell culture media) under suitable conditions for the production of said one or more recombinant polypeptides; and producing the one or more recombinant polypeptides, wherein the one or more recombinant polypeptides has a modulated glycosylation profile compared to recombinant polypeptides produced by mammalian cells that are not cultured in any of the cell culture media described herein. In some embodiments, "modulating the glycosylation profile" refers to increasing the relative percentage of a particular glycan species on the recombinant polypeptide. However, in other embodiments, the phrase "modulating the glycosylation profile" refers to decreasing the relative percentage of a particular glycan species on the recombinant polypeptide. Any relative percentage of any glycan species capable of addition to a recombinant polypeptide can be altered when produced in accordance with the methods disclosed herein.

In some embodiments, culturing mammalian cells that have been genetically engineered to produce recombinant polypeptides in any medium described herein (such as a lithium-containing, an ethanol-containing, and/or a fatty acid-containing cell culture media) modulated the amount of one or more of glycan species. Examples of glycan species include, without limitation, mannose-9-N-acetylglycosamine-2 (Man9), mannose-8-N-acetylglycosamine-2 (Man8), mannose-7-N-acetylglycosamine-2 (Man7), mannose-6-N-acetylglycosamine-2 (Man6), mannose-5-N-acetylglycosamine-2 (Man5), mannose-3-N-acetylglucosamine-2 (Man3), mannose-3-N-acetylglucosamine-3, mannose-3-N-acetylglucosamine-4 (G0), mannose-3-N-acetylglucosamine-3-fucose, mannose-3-N-acetylglucosamine-4-fucose (G0F), mannose-3-N-acetylglucosamine-4-galactose-1 (G1), mannose-3-N-acetylglucosamine-4-galactose-2 (G2), mannose-3-N-acetylglucosamine-4-galactose-1-fucose (G1F), mannose-3-

N-acetylglucosamine-4-galactose-2-fucose (G2F), mannose-3-N-acetylglucosamine-4-galactose-1-fucose-1-N-acetylneuraminic-1 (G1F-NANA), mannose-3-N-acetylglucosamine-4-galactose-2-fucose-1-N-acetylneuraminic-1 (G2F-NANA), and/or mannose-3-N-acetylglucosamine-4-galactose-2-fucose-1-N-acetylneuraminic-2 (G2F-2NANA) bound to the recombinant polypeptide. FIG. 1 depicts a schematic representation of major N-glycan linked species.

Alteration of glycan species on recombinant polypeptides can be separated and measured in accordance with any means known in the art such as, without limitation, high performance liquid chromatography (HPLC), normal-phase HPLC (NP), hydrophilic interaction liquid chromatography (HILIC), ion-exchange HPLC (IEX), weak anion exchange HPLC (WAX-HPLC), zwitterionic sulfobetaine (ZIC-HILIC), porous graphite carbon HPLC (PGC), capillary electrophoresis laser induced fluorescent (CE-LIF), matrix-assisted laser desorption/ionization time of flight (MALDI-TOF), electrospray ionization mass spectrometry (ESI-MS), liquid chromatography mass spectrometry (LC-MS) and tandem mass spectrometry (MS/MS).

In some embodiments, the culturing methods provided herein reduce a specific glycan species normalized or relative to the total glycan pool on a recombinant polypeptide. For example, in some embodiments, the method modulates (e.g. decreases) one or more specific glycan species on the recombinant polypeptides by any of about 1% to about 2%, about 1% to about 3%, about 1% to about 4%, about 1% to about 5%, about 2.5% to about 5%, about 2.5% to about 7.5%, about 5% to about 7.5%, about 5% to about 10%, about 1 to about 15%, about 7.5% to about 12.5%, about 7.5% to about 15%, about 7.5% to about 17.5%, about 10% to about 12.5%, about 10% to about 15%, about 10% to about 17.5%, about 10% to about 20%, about 12.5% to about 15%, about 12.5% to about 17.5%, about 12.5% to about 20%, about 12.5% to about 22.5%, about 15% to about 17.5%, about 15% to about 20%, about 15% to about 22.5%, about 15% to about 25%, about 17.5% to about 20%, about 17.5% to about 22.5%, about 17.5% to about 25%, about 17.5% to about 27.5%, about 20% to about 22.5%, about 20% to about 25%, about 20% to about 27.5%, about 20% to about 30%, about 22.5% to about 25%, about 22.5% to about 27.5%, about 22.5% to about 30%, about 22.5% to about 32.5%, about 25% to about 27.5%, about 25% to about 30%, about 25% to about 32.5%, or about 25% to about 35%, or at least any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%, inclusive of values falling in between these percentages, compared to the amount of the glycan species of recombinant polypeptides produced by mammalian cells that are not cultured in the media disclosed herein (such as a lithium-containing, an ethanol-containing, and/or a fatty acid-containing cell culture media) and in accordance with the methods described herein. In some embodiments, the glycan species is Man5, G0, or G0F.

In some embodiments, the culturing methods provided herein increase a specific glycan species normalized or relative to the total glycan pool on a recombinant polypeptide. For example, in yet other embodiments, the method increases one or more specific glycan species by any of about 1% to about 2%, about 1% to about 3%, about 1% to about 4%, about 1% to about 5%, about 2.5% to about 5%, about 2.5% to about 7.5%, about 5% to about 7.5%, about 5% to about 10%, about 1 to about 15%, about 7.5% to about 12.5%, about 7.5% to about 15%, about 7.5% to about 17.5%, about 10% to about 12.5%, about 10% to about 15%, about 10% to about 17.5%, about 10% to about 20%, about 12.5% to about 15%, about 12.5% to about 17.5%, about 12.5% to about 20%, about 12.5% to about 22.5%, about 15% to about 17.5%, about 15% to about 20%, about 15% to about 22.5%, about 15% to about 25%, about 17.5% to about 20%, about 17.5% to about 22.5%, about 17.5% to about 25%, about 17.5% to about 25%.7, about 20% to about 22.5%, about 20% to about 25%, about 20% to about 27.5%, about 20% to about 30%, about 22.5% to about 25%, about 22.5% to about 27.5%, about 22.5% to about 30%, about 22.5% to about 32.5%, about 25% to about 27.5%, about 25% to about 30%, about 25% to about 32.5%, or about 25% to about 35%, or at least any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%, inclusive of values falling in between these percentages, compared to the amount of the glycan species of recombinant polypeptides produced by mammalian cells that are not cultured in the media disclosed herein (such as a lithium-containing, an ethanol-containing, and/or a fatty acid-containing cell culture media) and in accordance with the methods described herein.

In some embodiments, culturing mammalian cells genetically engineered to produce one or more recombinant polypeptides in any of the media disclosed herein according the methods described herein modulates (e.g. reduces) the amount of terminal mannose glycan species in comparison to the total sum of all glycan species on the polypeptide. As used herein, the phrase "terminal mannose glycan species" refers to one or more of mannose-5-N-acetylglycosamine-2 (Man5), mannose-6-N-acetylglycosamine-2 (Man6), mannose-7-N-acetylglycosamine-2 (Man7), mannose-8-N-acetylglycosamine-2 (Man8) and/or mannose-9-N-acetylglycosamine-2 (Man9) moieties.

As such, for recombinant polypeptides produced in accordance with any of the methods described herein using any of the cell culture media disclosed herein (such as a lithium-containing, an ethanol-containing, and/or a fatty acid-containing cell culture media), the ratio of the terminal mannose glycan species to the total sum of glycan species on the polypeptide can be modulated (e.g., decreased) by about 30% to about 70%, about 35% to about 65%, about 40% to about 60%, about 45% to about 55%, or about 47.5% to about 52.5%, such as any of about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% or more.

In some embodiments, culturing mammalian cells genetically engineered to produce one or more recombinant polypeptides in any of the ethanol-containing media disclosed herein according the methods described herein modulates the amount of any one of G1F, G2F, and/or G0F glycan species in comparison to the total sum of all glycan species on the polypeptide. As such, for recombinant polypeptides produced in accordance with any of the methods described herein using any of the cell culture media disclosed herein (such as a lithium-containing, an ethanol-containing, and/or a fatty acid-containing cell culture media), the ratio any one of G1F, G2F, and/or G0F glycan species to the total sum of glycan species on the polypeptide can be modulated by about 30% to about 70%, about 35% to about 65%, about 40% to about 60%, about 45% to about 55%, or about 47.5% to about 52.5%, such as any of about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% or more.

C. Methods for Modulating High or Low Molecular Weight Species

In further aspects, provided herein are methods for modulating (e.g. reducing) the amount of high or low molecular weight species of one or more recombinant polypeptides produced by an engineered mammalian cell. The method entails culturing a mammalian cell in any of the cell culture media described herein (such as a lithium-containing, an ethanol-containing, and/or a fatty acid-containing cell culture media) under suitable conditions for the production of said one or more recombinant polypeptides; and producing the one or more recombinant polypeptides, wherein the recombinant polypeptides have reduced amounts of high or low molecular weight species compared to recombinant polypeptides produced by recombinant mammalian cells that are not cultured in any of the cell culture media of the present invention.

"High molecular weight species" (HMWS) as used in the context of the present invention means the development of any particle which consists of more than one subunit of a recombinant polypeptide, also including oligomers, such as e.g. dimers, trimers, tetramers, pentamers and the like. HMWS can also consist of more than 2 subunits, such as any of 3, 4, 5, 6, 7, 8, or more. HMWS can be of different sizes, which have a mass greater than that of the fully assembled recombinant polypeptide.

"Low molecular weight species" (LMWS) as used in the context of the present invention means the development of any particle which consists of one or more subunit of a recombinant polypeptide, also including oligomers, such as e.g. dimers, trimers, tetramers, pentamers and the like. LMWS can comprise of polypeptide fragments that are not completely assembled and/or folded. LMWS can be of different sizes, which have a mass less than that of the fully assembled recombinant polypeptide.

The amount of high or low molecular weight species of the recombinant polypeptides can be measured in accordance with any means known in the art such as, without limitation, size exclusion chromatography (SEC), analytical ultra-centrifugation (AUC), dynamic or static light-scattering spectroscopy (DLS), differential scanning calorimetry (DSC) or asymmetric flow field flow fractionation (AF4).

In some embodiments, the cell culture methods disclosed herein modulate (e.g. decrease) the amount of HMW species compared to total detected polypeptide molecular weight variants by any of about 1% to about 2%, about 1% to about 3%, about 1% to about 4%, about 1% to about 5%, about 2.5% to about 5%, about 2.5% to about 7.5%, about 5% to about 7.5%, about 5% to about 10%, about 1 to about 15%, about 7.5% to about 12.5%, about 7.5% to about 15%, about 7.5% to about 17.5%, about 10% to about 12.5%, about 10% to about 15%, about 10% to about 17.5%, about 10% to about 20%, about 12.5% to about 15%, about 12.5% to about 17.5%, about 12.5% to about 20%, about 15% to about 17.5%, about 15% to about 20%, about 17.5% to about 20%, about 17.5% to about 22.5%, about 17.5% to about 25%, about 20% to about 22.5%, about 20% to about 25%, about 22.5% to about 25%, or at least any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% or more, inclusive of values falling in between these percentages, compared to the amount of HMW species of recombinant polypeptides produced by mammalian cells that are not cultured in a media disclosed herein (such as a lithium-containing, an ethanol-containing, and/or a fatty acid-containing cell culture media) and in accordance with the methods described herein.

In other embodiments, the cell culture methods disclosed herein modulate (e.g. decrease) the amount of LMW species compared to total detected polypeptide molecular weight variants by any of about 1% to about 5%, about 2.5% to about 7.5%, about 5% to about 7.5%, about 5% to about 10%, about 7.5% to about 12.5%, about 7.5% to about 15%, about 7.5% to about 17.5%, about 10% to about 15%, about 10% to about 17.5%, about 10% to about 20%, about 12.5% to about 17.5%, about 12.5% to about 20%, about 12.5% to about 22.5%, about 15% to about 20%, about 15% to about 22.5%, about 15% to about 25%, about 17.5% to about 22.5%, about 17.5% to about 25%, about 17.5% to about 27.5%, about 20% to about 25%, about 20% to about 27.5%, about 20% to about 30%, about 22.5% to about 27.5%, about 22.5% to about 30%, about 22.5% to about 32.5%, about 25% to about 30%, about 25% to about 32.5%, about 25% to about 35%, about 27.5% to about 37.5%, about 30% to about 40%, about 32.5% to about 44.5%, about 35% to about 45%, about 37.5% to about 47.5%, about 40% to about 50%, about 42.5% to about 52.5%, about 45% to about 55%, about 47.5% to about 57.5%, about 50% to about 60%, about 52.5% to about 62.5%, about 55% to about 65%, about 57.5% to about 67.5%, about 60% to about 70%, about 62.5% to about 72.5%, or about 65% to about 75% or at least any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75% or more, inclusive of values falling in between these percentages, compared to the amount of LMW species of recombinant polypeptides produced by mammalian cells that are not cultured in a media disclosed herein (such as a lithium-containing, an ethanol-containing, and/or a fatty acid-containing cell culture media) and in accordance with the methods described herein.

D. Methods for Modulating the Amount of Acidic or Basic Charge Species

In further aspects, provided herein are methods for modulating (e.g. reducing) the amount of acidic or basic charge species of one or more recombinant polypeptides produced by an engineered mammalian cell. The method entails culturing a mammalian cell in any of the cell culture media described herein under suitable conditions for the production of said one or more recombinant polypeptides; and producing the one or more recombinant polypeptides, wherein the recombinant polypeptides have reduced amounts of acidic or basic charge species compared to recombinant polypeptides produced by mammalian cells that are not cultured in any of the cell culture media described herein (such as a lithium-containing, an ethanol-containing, and/or a fatty acid-containing cell culture media).

As used herein, or "acidic charge species" or "acidic charge variants" refer to the percentage of recombinantly produced proteins in a mammalian cell culture that bear acidic charges compared to the total polypeptide charge variants of the total population of recombinantly produced proteins. Similarly, "basic charge species" or "basic charge variants," as used herein, refer to the percentage of recombinantly produced proteins in a mammalian cell culture that bear basic charges compared to the total polypeptide charge variants of the total population of recombinantly produced proteins.

In some embodiments, the cell culture methods disclosed herein modulate (e.g. decrease) the amount of acidic charge species compared to total detected polypeptide charge variants by any of about 1% to about 2%, about 1% to about 3%, about 1% to about 4%, about 1% to about 5%, about 2.5% to about 5%, about 2.5% to about 7.5%, about 5% to about 7.5%, about 5% to about 10%, about 1 to about 15%, about 7.5% to about 12.5%, about 7.5% to about 15%, about 10% to about 12.5%, about 10% to about 15%, or about 12.5% to about 15%, or at least any of 1%, 2%, 3%, 4%, 5%, 6%, 7%, 8%, 9%, 10%, 11%, 12%, 13%, 14%, or 15%, or more, inclusive of values falling in between these percentages, compared to the amount of acidic charge species of recombinant polypeptides produced by mammalian cells that are not cultured in a media disclosed herein (such as a lithium-containing, an ethanol-containing, and/or a fatty acid-containing cell culture media) and in accordance with the methods described herein.

In other embodiments, the cell culture methods disclosed herein modulate (e.g. decrease) the amount of basic charge species compared to total detected polypeptide charge variants by any of about 1% to about 2%, about 1% to about 3%, about 1% to about 4%, about 1% to about 5%, about 2.5% to about 5%, about 2.5% to about 7.5%, about 5% to about 7.5%, about 5% to about 10%, about 1 to about 15%, about 7.5% to about 12.5%, about 7.5% to about 15%, about 10% to about 12.5%, about 10% to about 15%, or about 12.5% to about 15%, or at least any of 1%, 2%, 3%, 4%, 5%, 6%, 7%, 8%, 9%, 10%, 11%, 12%, 13%, 14%, or 15%, or more, inclusive of values falling in between these percentages, compared to the amount of basic charge species of recombinant polypeptides produced by mammalian cells that are not cultured in a media disclosed herein (such as a lithium-containing, an ethanol-containing, and/or a fatty acid-containing cell culture media) and in accordance with the methods described herein.

V. Kits

In addition, the present invention includes a kit for culturing mammalian cells in accordance with any of the methods disclosed herein. The kits can contain one or more of a mammalian cell culture basal medium and/or a mammalian cell culture feed medium. Further, the kits can additionally contain one or more of a source of lithium ions, ethanol, and one or more fatty acids. The kit can also include written instructions for using the kit, such as instructions for making any of the mammalian cell culture media disclosed herein as well as instructions for using a medium to culture mammalian cells (such as, culturing mammalian cells genetically engineered for the production of one or more recombinant polypeptides).

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

EXAMPLES

Example 1: Addition of Lithium to Cell Culture Medium Improves Production and Quality of Recombinant Polypeptides This Example shows the effect of lithium addition to culture media with respect to production of a recombinant antibody.

I. Determination of Cytotoxicity

Lithium chloride cytotoxicity to CHO.DXB11 cells was determined by a single dose bolus spike. 4 mL of CHO cells at 6 e6/mL cellular density were seeded into 6 well deep plates, mixed at 150 RPM, and spiked with lithium chloride to a working concentration range of 5 mM to 250 mM. Cell growth rate and cell viability were negatively affected when single dose spiking of lithium chloride exceeded 10 mM.

II. Addition of Lithium Using Microscale Bioreactors for Monoclonal Antibody Production To determine if LiCl altered mAb properties it was incorporated into fully defined and synthetic feed media and fed daily in a fed-batch process using micro—(15 mL working volume) bioreactors.

Materials and Methods

Monoclonal antibody 1 (mAb 1) is a monoclonal antibody produced using recombinant DNA technology. The expression vector is fully synthetic with both heavy- and light-chain gene sequences regulated by strong constitutive promoters. Gene sequences were confirmed by DNA sequencing. The expression vector was linearized by restriction enzymes and stably transfected into CHO.DXB11 cells by electroporation.

Single cell cloning was performed after gene amplification. Select single cell clones were expanded and cryopreserved.

Titer was measured using a Thermo Ultimate 3000 Series HPLC with the detection wavelength set at 280 nm. Mobile phase A contained sodium phosphate and sodium chloride with mobile phase B containing acetic acid and magnesium chloride. An Applied Biosystems POROS A20 column was used and analysis was performed using the Thermo Chromeleon software. Purified antibody was used as the standard for quantitation.

Glycosylation species were measured with the Thermo Ultimate 3000 Series HPLC and the Thermo Q Exactive Mass Spectrometer. Mobile phase A consists of formic acid and trifluoroacetic acid in water with mobile phase B consisting of formic acid and trifluoroacetic acid in acetonitrile. An Agilent PLRP-S 1000A 5 µM column was used and analysis was performed using the Thermo Excalibur software in conjunction with the Thermo Protein Deconvolution software.

LiCl was fed daily to increase working bioreactor concentrations between 0.11 mM and 1.11 mM. Calculated cumulative cell culture concentration (concentration in vessel at time of cell harvest) of lithium ranged between 1 mM-10 mM. Bioreactor physical conditions were maintained at a pH of 7.0±0.2, dissolved oxygen at 30% air saturation and temperatures of 37° C. or 35° C. for logarithmic cellular growth phase and shifted to 31° C. during cellular production phase (temperature was shifted one day before max viable cell density was reached). Basal and feed media are fully synthetic and chemically defined containing no animal derived components.

Results

Figure 2:
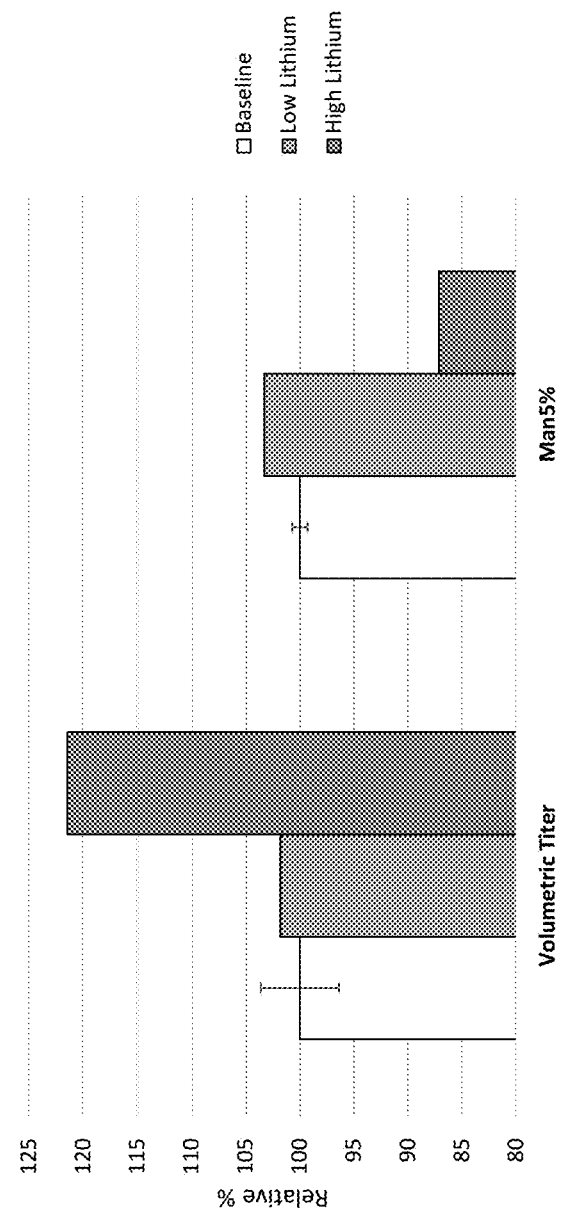
FIG. 2 depicts impact on titer and Man5% glycan species. Titer is reported as volumetric titer and Man5% glycan species as percent of the total detected glycan pool. Values are normalized to baseline. Lithium was fed daily to increase bioreactor concentration by 0.11 mM (low lithium) and 1.11 mM (high lithium) in a 12 day fed-batch process. Higher doses of lithium increased titer over 21% and reduced Man5% by over 13% compared to baseline

Lithium was shown to increase antibody titer at the high end of the concentrations used (FIG. 2). Higher doses of lithium increased titer over 21% compared to baseline. Furthermore, higher concentrations of lithium reduced Man5 glycan species by over 13% (FIG. 2).

III. Addition of Lithium Using Microscale Bioreactors for Monoclonal Antibody Production in a Design of Experiment (DOE) Study Lithium was used in design of experiments (DOE) created with custom DOE design using JMP statistical software (World Wide Web.jmp.com/en_us/home.html). Lithium was fed daily to increase bioreactor working concentrations by 0.5 mM or 1 mM in a 12 day fed-batch process. A response model was created using standard least squares to determine the significance of response from lithium supplementation. Potential interactions with other supplemented components were also considered.

Figure 3:
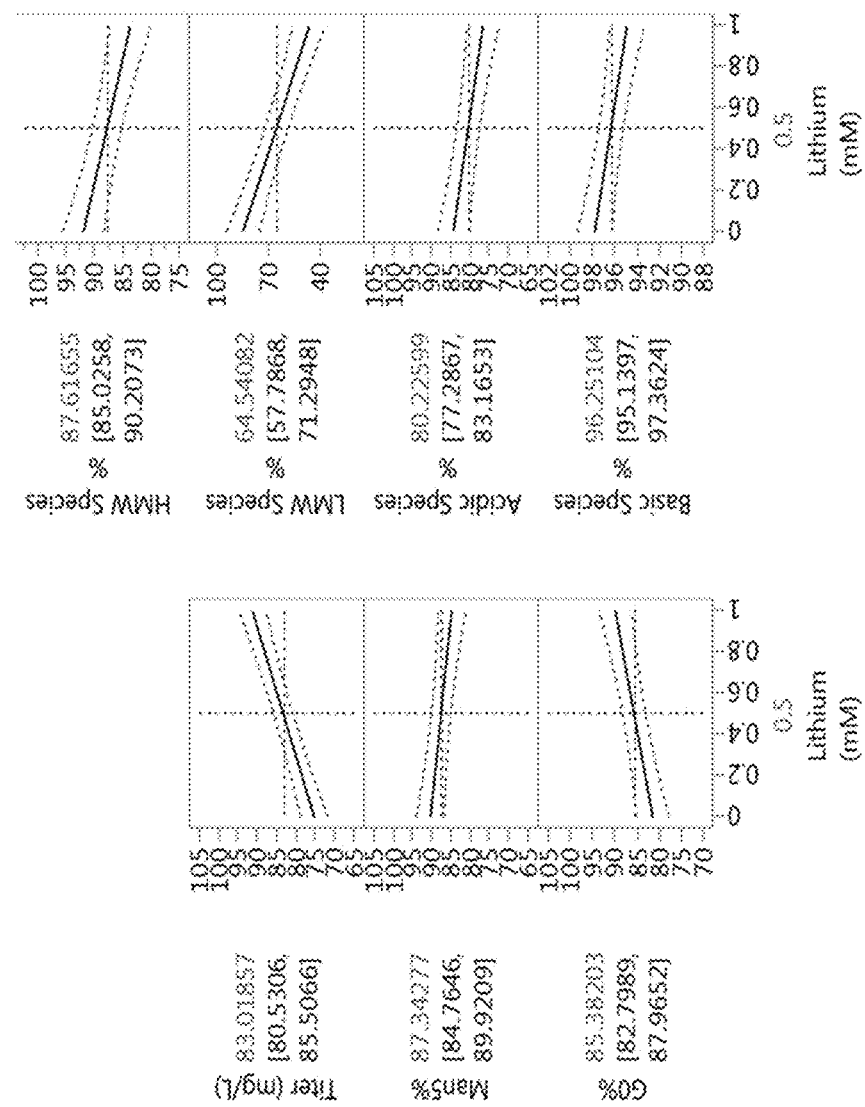
FIG. 3 depicts the prediction response profile for Titer, Man5%, G0%, HMW %, LMW %, Acidic % and Basic % species using 2 L bench scale bioreactors. Lithium was fed daily to increase bioreactor concentrations by 1 mM in a 14 day fed-batch process. Values are normalized to highest observed value for each response. Dotted lines represent confidence intervals of each response.

FIG. 3 depicts the results of the DOE analysis. Titer, Man5%, G0%, HMW %, LMW %, Acidic % and Basic % species were assessed. The prediction profile shows how the model changes as individual factors are varied in order to gauge the model's sensitivity to changes in those factors. As shown below in Table 1, addition of 1 mM lithium increased titer by over 20%, decreased Man5 glycan species by over 6%, decreased high and low molecular weight species by over 9% and 46%, respectively, and also decreased acidic and basic charge variant species by over 9% and 3%, respectively.

TABLE 1

Change in response values extracted from the prediction profile of Titer, Man5%, G0%, HMW %, LMW %, Acidic % and Basic % species.

|  | Titer | Man5% | G0% | HMW % | LMW % | Acidic % | Basic % |
|---|---|---|---|---|---|---|---|
| 0.5 mM Lithium | +10.7% | −3.1% | +5.2% | −4.5% | −23.0% | −4.5% | −1.5% |
| 1.0 mM Lithium | +21.3% | −6.3% | +10.4% | −9.1% | −46.0% | −9.1% | −3.0% |

IV. Addition of Lithium Using Microscale Bioreactors for Monoclonal Antibody Production in a Design of Experiment (DOE) Study Using Alternate Variables Lithium was used in design of experiment, as described above, using alternative process conditions. Physical conditions were altered by changing temperature and pH set points. Feed formulations were modified to include additional amino acids and trace elements. Lithium was fed daily to increase bioreactor working concentrations by 0.5 mM or 1 mM in a 13 day fed-batch process. A response model was created using standard least squares in order to determine the significance of response from lithium supplementation. Potential interactions with other supplemented components were also considered.

Figure 4:
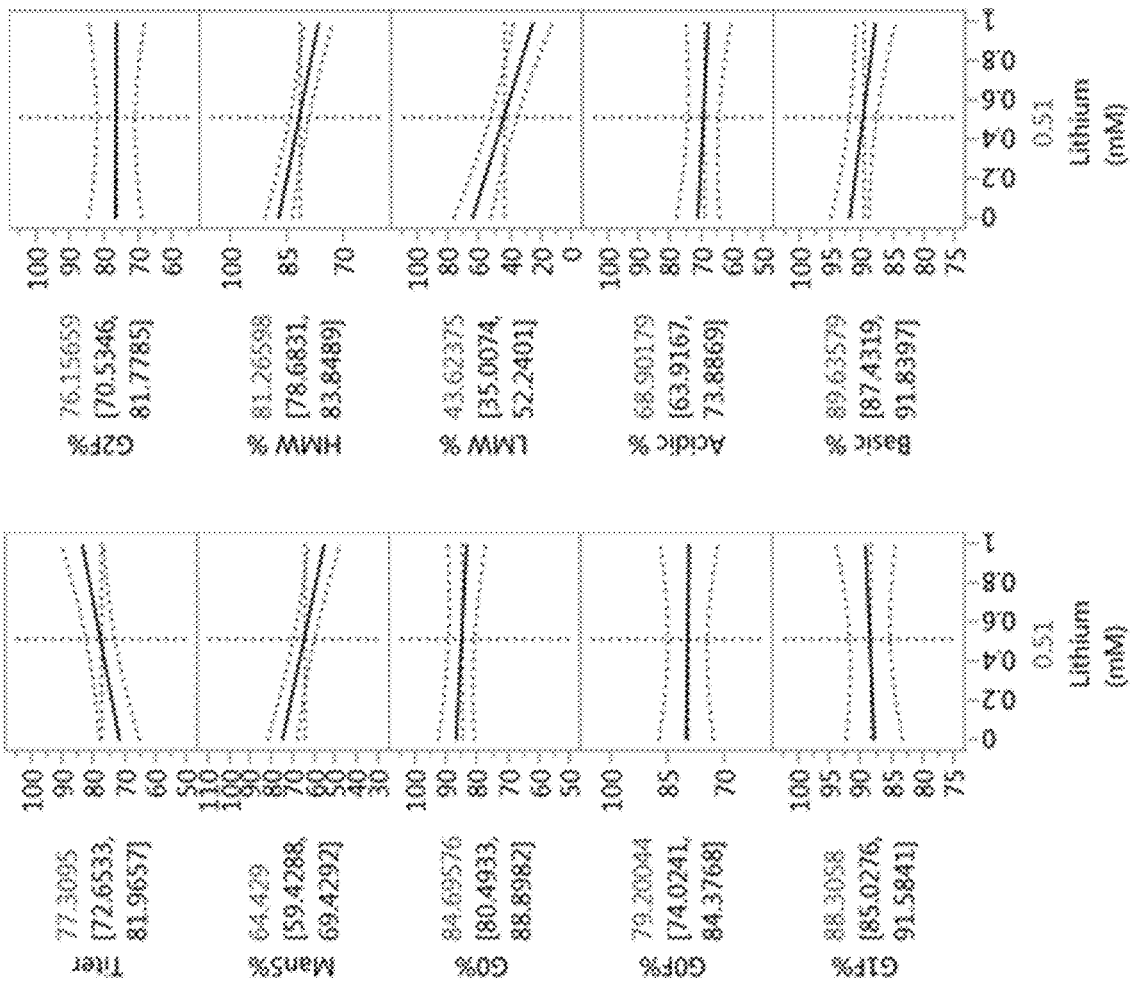
FIG. 4 depicts the prediction response profile for Titer, Man5%, G0%, G0F %, G1F %, G2F %, HMW %, LMW %, Acidic % and Basic % species. Physical conditions were altered by changing temperature and pH set points. Lithium was fed daily to increase bioreactor working concentration by 0.5 mM or 1 mM in a 12 day fed-batch process. Response values are normalized to the highest observed value for each response. Dotted lines represent confidence intervals of each response.

Results are shown in FIG. 4. Titer, Man5%, G0%, G0F %, G1F %, G2F %, HMW %, LMW %, Acidic % and Basic % species were assessed. The change in response values extracted from the prediction profile is shown in Table 2 below. At 1 mM concentration, lithium increased titer by almost 17%, decreased Man5 glycan variants by more the 26%, decreased high and low molecular weight species by more than 12% and more than 61%, respectively, and decreased acidic and basic charge variants by more than 4% compared to baseline.

TABLE 2

Change in response values extracted from the prediction profile of Titer, Man5%, G0%, G0F %, G1F %, G2F %, HMW %, LMW %, Acidic % and Basic % species.

|  | Titer | Man5% | G0% | G0F % | G1F % | G2F % | HMW % | LMW % | Acidic % | Basic % |
|---|---|---|---|---|---|---|---|---|---|---|
| 0.5 mM Lithium | +8.5% | −13.2% | −2.0% | −0.5% | +0.8% | −0.3% | −6.1% | −30.9% | −2.4% | −2.3% |
| 1.0 mM Lithium | +16.9% | −26.4% | −4.0% | −0.9% | +1.6% | −0.6% | −12.2% | −61.8% | −4.8% | −4.5% |

Figure 5:
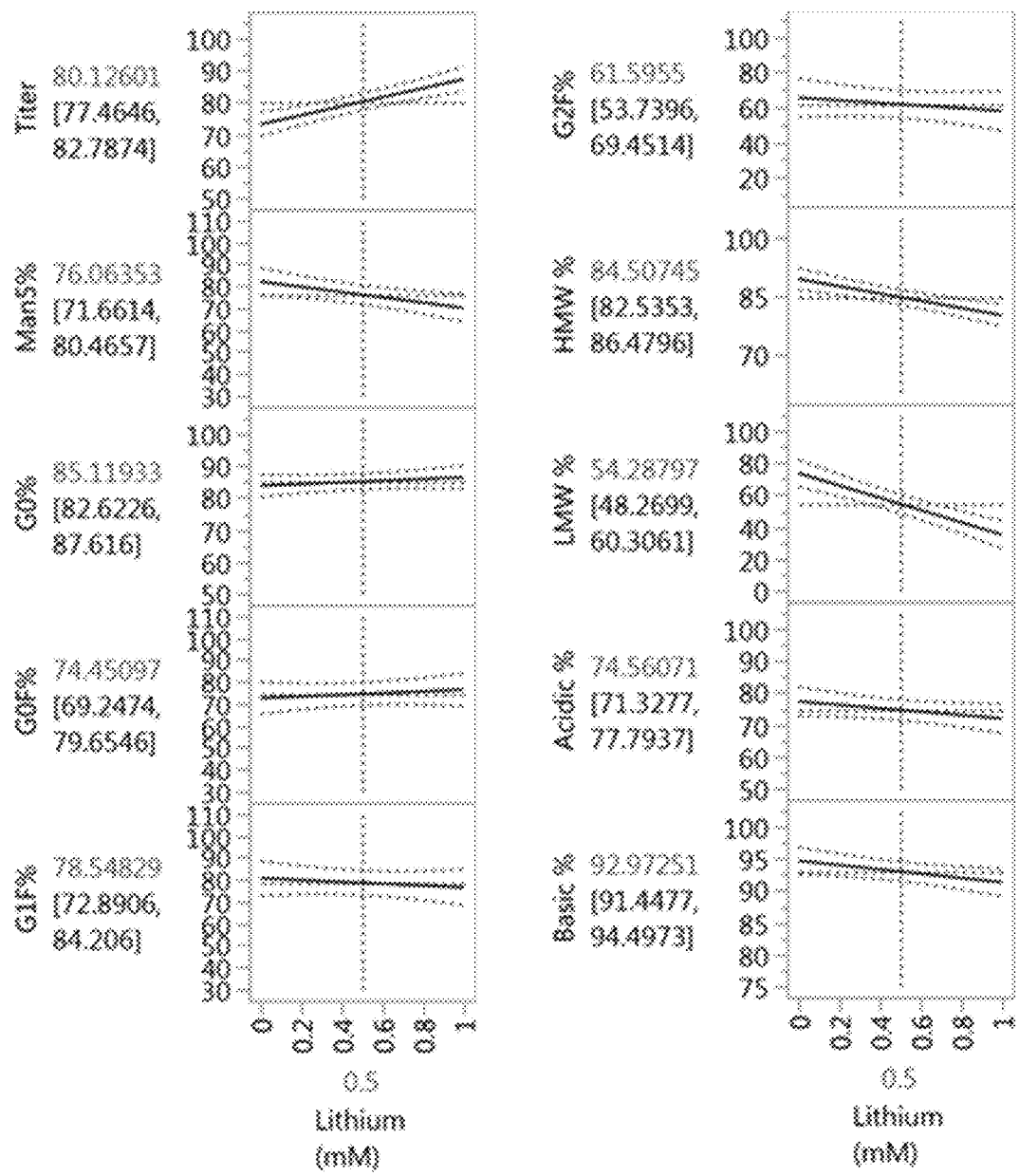
FIG. 5 depicts the combined prediction response profile of Titer, Man5%, G0%, G0F %, G1F %, G2F %, HMW %, LMW %, Acidic % and Basic % species. Lithium was fed daily to increase bioreactor working concentrations by 0.5 mM or 1 mM in a 12 day fed-batch process. Response values are normalized to the highest observed value for each response. Dotted lines represent confidence intervals of each response.

DOE experimental results from the two analyses described above were combined into one prediction model using a total of 48 independent bioreactor conditions. By combining data sets, confidence intervals tighten and p-values decrease leading to a higher significance of response. The prediction response profile for this combined data is shown in FIG. 5 and the change in response values extracted from the prediction profile are shown below in Table 3. As shown, at 1 mM concentration, lithium increased titer by almost 20%, decreased Man5 glycan variants by more than 14%, decreased high and low molecular weight species by more than 10% and more than 52%, respectively, and decreased acidic and basic charge variants by more than 6% and 3%, respectively.

TABLE 3

Change in response values extracted from the prediction profile of Titer, Man5%, G0%, G0F %, G1F %, G2F %, HMW %, LMW %, Acidic % and Basic % species.

|  | Titer | Man5% | G0% | G0F % | G1F % | G2F % | HMW % | LMW % | Acidic % | Basic % |
|---|---|---|---|---|---|---|---|---|---|---|
| 0.5 mM Lithium | +9.7% | −7.3% | −1.6% | +2.6% | −2.6% | −5.8% | −5.2% | −26.2% | −3.4% | −1.8% |
| 1.0 mM Lithium | +19.4% | −14.6% | +3.2% | +5.3% | −5.1% | −11.5% | −10.4% | −52.4% | −6.9% | −3.6% |

V. Use of Lithium-Supplemented Media for Production of a Different Monoclonal Antibody Monoclonal antibody 2 (mAb 2) is a monoclonal antibody produced using recombinant DNA technology. The expression vector is fully synthetic with both heavy- and light-chain gene sequences regulated by strong constitutive promoters. Gene sequences were confirmed by DNA sequencing. The expression vector was linearized by restriction enzymes and stably transfected into CHO.DG44 cells by electroporation. Two rounds of single cell cloning were performed. Single cell clones were expanded and cryopreserved.

Figure 6:
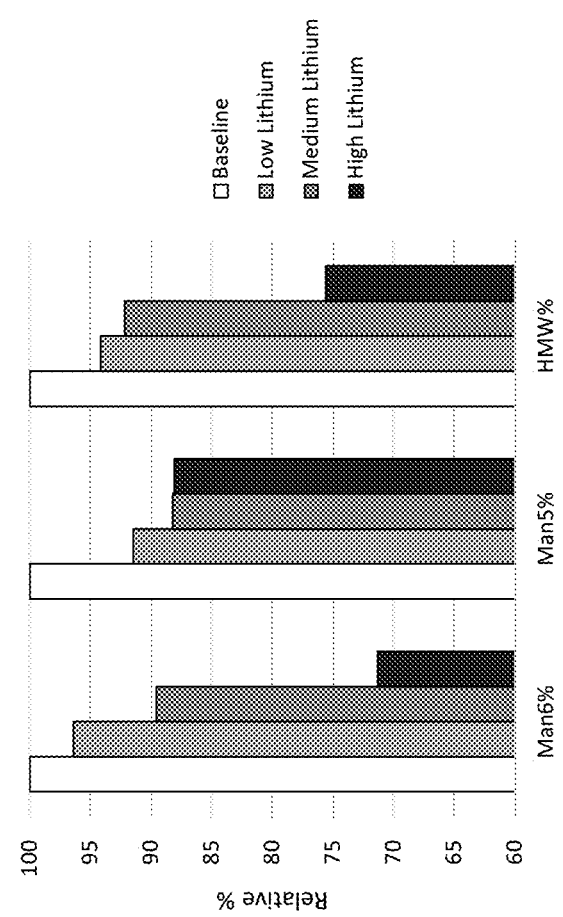
FIG. 6 depicts impact on Man6%, Man5% and HMW % levels using a CHO DG44 host producing mAb2. Man6% and Man5% glycan species are reported as a percent of the total detected glycan pool. HMW % is reported as a percent of the total detected polypeptide molecular weight variants. Values are normalized to baseline. Lithium was fed daily to increase bioreactor concentrations by 0.11 mM (Low Lithium), 0.44 mM (Medium Lithium) and 1.11 mM (High Lithium) in a 13 day fed-batch process. High lithium reduced Man6% and Man5% glycan species by 29% and 12%, respectively over baseline. High lithium reduced high molecular weight species by 24% compared to baseline.

Lithium was tested using a different CHO host (CHO DG44) which produces monoclonal antibody #2 (mAb2). Cell culture and monoclonal antibody production was performed as described above. Cells were grown in microscale bioreactors and lithium was fed daily to increase bioreactor concentrations by 0.11 mM (Low Li), 0.44 mM (Medium Li) and 1.11 mM (High Li) in a 13 day fed-batch process. Results indicated that supplementing lithium into the cell culture media reduced Man6% glycan levels (FIG. 6) and Man5% glycan levels (FIG. 6) by 29% and 12%, respectively over baseline. Further, higher lithium concentrations reduced high molecular weight species 24% over baseline (FIG. 6).

Example 2: Addition of Ethanol to Cell Culture Medium Improves Production of Recombinant Polypeptides Previously, an ethanol-based cholesterol supplement was developed in order to cultivate cholesterol-dependent NS0 cells in a linear, low-density polypropylene-based disposable bioreactor system. This ethanol-based supplement contained cholesterol, oleic acid and linoleic acid (Tao et al., Biotechnol Lett., 2012; 34(8):1453-8). This Example investigated the use of ethanol as a solubilizing agent for various fatty acids for the production of mAb products.

I. Determination of Cytotoxicity

Ethanol cytotoxicity to CHO.DXB11 cells was determined by daily feed dosing. 4 mL of CHO cells at 3 e6/mL cellular density were seeded into 6 well deep plates, mixed at 150 RPM, and fed once daily with ethanol ranging from 0.1% to 0.4% volume to volume (v/v). Cell growth rate and cell viability were negatively affected when daily ethanol feeding exceeded 0.3% v/v.

II. Addition of Ethanol Using Microscale Bioreactors for Monoclonal Antibody Production To determine if ethanol altered mAb properties it was incorporated into fully defined and synthetic feed media and fed daily in a fed-batch process using micro—(15 mL working volume) bioreactors.

Materials and Methods:

Antibody production was performed as described above for mAb 1.

Cell line A is a CHO.DXB11 derived clone producing mAb 1. Cell line B is a different CHO.DXB11 derived clone producing mAb1. The expression cassette is identical between the two cell lines.

Ethanol was fed daily 0.0% or 0.057% v/v using microscale bioreactors and two different cellular clones producing mAb1. Calculated cumulative cell culture concentration (concentration in vessel at time of cell harvest) of ethanol ranged between 0.0%-0.51% v/v. Bioreactor physical conditions were maintained at a pH of 7.0±0.2, dissolved oxygen at 30% air saturation and a temperature of 35° C. during logarithmic cellular growth phase and shifted to 31° C. during cellular production phase (temperature was shifted one day before max viable cell density was reached). Basal and feed media were fully synthetic and chemically defined containing no animal derived components.

Figure 7:
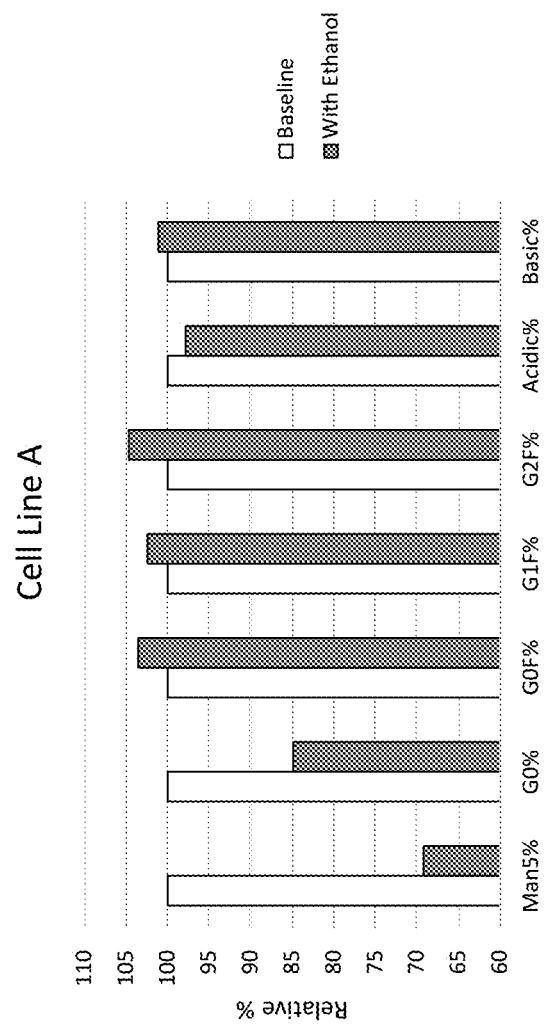
FIG. 7 depicts the impact on Man5%, G0%, G0F %, G1F %, G2F %, Acidic % and Basic % species using a CHO.DXB11 host (Cell Line A) producing mAb1. Man5%, G0%, G0F %, G1F % and G2F % glycan species are reported as a percent of the total detected glycan pool. Acidic % and Basic % are reported as a percent of the total detected polypeptide charge species variants. Values are normalized to baseline. Ethanol was fed daily to increase bioreactor concentrations by 0.0% (Baseline) and 0.057% (with Ethanol) v/v in a 12 day fed-batch process.
Figure 8:
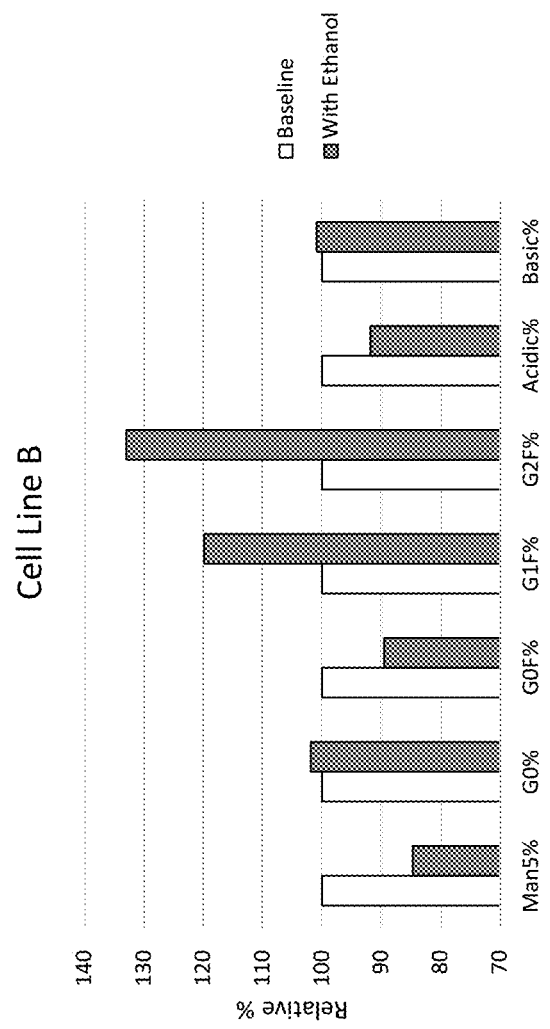
FIG. 8 depicts the impact on Man5%, G0%, G0F %, G1F %, G2F %, Acidic % and Basic % species using a CHO.DXB11 host (Cell Line B) producing mAb1. Man5%, G0%, G0F %, G1F % and G2F % glycan species are reported as a percent of the total detected glycan pool. Acidic % and Basic % are reported as a percent of the total detected polypeptide charge species variants. Values are normalized to baseline. Ethanol was fed daily to increase bioreactor concentrations by 0.0% (Baseline) and 0.057% (with Ethanol) v/v in a 12 day fed-batch process.

Results:

Ethanol supplementation was observed to alter glycosylation profile, alter high molecular weight and low molecular weight species and alter acidic and basic charge species. As shown in FIG. 7 and FIG. 8, ethanol decreased overall Man5% glycan species in both cell lines used, whereas the effect on G0% and G0F % glycan species varied with respect to the cell line (FIG. 7 and FIG. 8). Further, ethanol increased overall G1F % and G2F % glycan species varied with respect to both cell lines used (FIG. 7 and FIG. 8). Moreover, ethanol decreased the relative amount of acidic charge variants while slightly increasing the relative percentage of basic charge variants when compared to the total detected charge species variants for both cell lines tested (FIG. 7 and FIG. 8).

Figure 9:
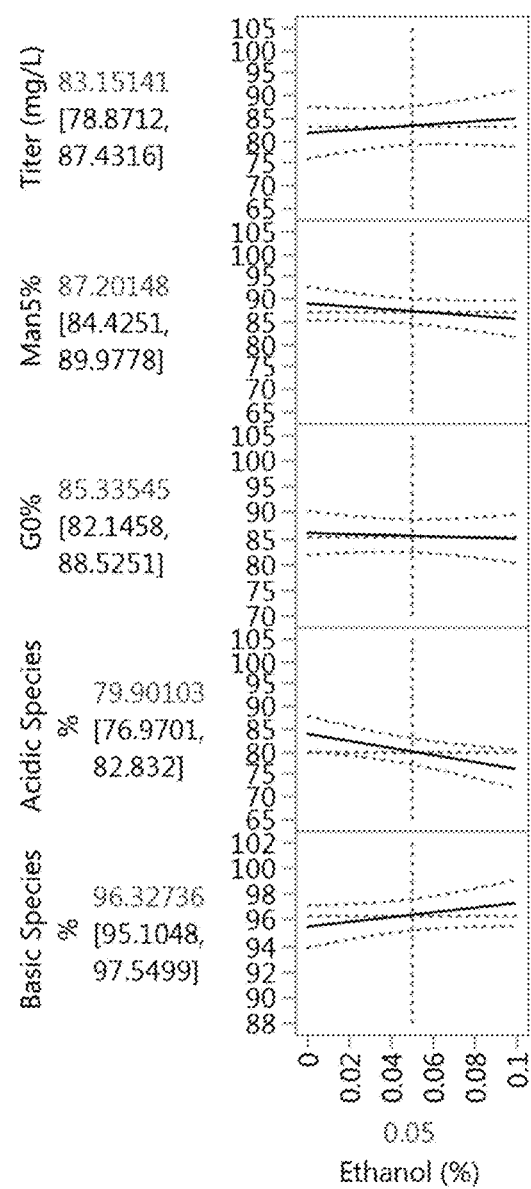
FIG. 9 depicts the prediction response profile of Titer, Man5%, G0%, Acidic % and Basic % species. Ethanol was fed daily to increase bioreactor concentrations by 0.0% or 0.1% v/v in a 12 day fed-batch process. Response values are normalized to the highest observed value for each response. Dotted lines represent confidence intervals of each response.

III. Addition of Ethanol Using Microscale Bioreactors for Monoclonal Antibody Production in a Design of Experiment (DOE) Study Ethanol was used in design of experiments (DOE) created with custom DOE design using JMP statistical software (World Wide Web.jmp.com/en_us/home.html). A response model was created using standard least squares to determine the significance of response from ethanol supplementation. Potential interactions with other supplemented components were also considered. Ethanol was fed daily between 0.0% and 0.1% using microscale bioreactors. FIG. 9 is a prediction response profile for Titer, Man5%, G0%, Acidic % and Basic % species while the change in response values for each of these is shown depicted in Table 4 below.

TABLE 4

Change in response values extracted from the prediction profile of Titer, Man5%, G0%, Acidic % and Basic % species. Ethanol was fed daily to increase bioreactor working concentrations by 0.05% and 0.1% v/v in a 12 day fed-batch process.

|  | Titer | Man5% | G0% | Acidic % | Basic % |
| --- | --- | --- | --- | --- | --- |
| 0.05% v/v Ethanol | +2.0% | −1.9% | −0.7% | −4.7% | +1.0% |
| 0.1% v/v Ethanol | +3.9% | −3.8% | −1.3% | −9.3% | +1.9% |

IV. Addition of Ethanol Using Bench-Scale Bioreactors

Materials and Methods:

Antibody production was performed as described above for mAb 1.

Ethanol was fed daily 0.072% (Low Ethanol) or 0.144% (High Ethanol) v/v. Calculated cumulative cell culture concentration (concentration in vessel at time of cell harvest) of ethanol ranged between 0.79%-1.58% v/v. Bioreactor physical conditions were maintained at a pH of 7.0±0.2, dissolved oxygen maintained at 30% of air saturation, temperature of 35° C. during logarithmic cellular growth phase and shifted to 31° C. during cellular production phase (temperature was shifted one day before max viable cell density was reached). Basal and feed media were fully synthetic and chemically defined containing no animal derived components.

Results

Figure 10:
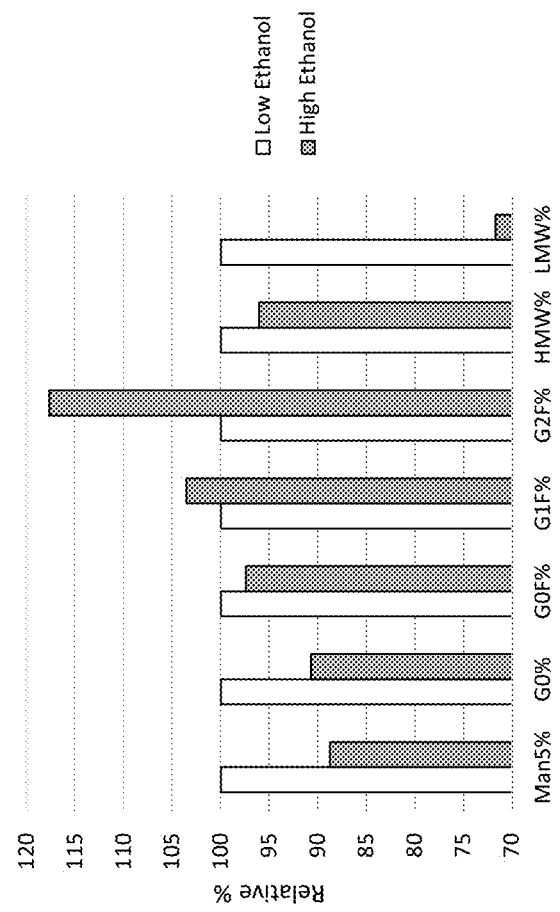
FIG. 10 depicts the impact on Man5%, G0%, G0F %, G1F %, G2F %, HMW % and LMW % species using bench-scale bioreactors. Man5%, G0%, G0F %, G1F % and G2F % glycan species are reported as a percent of the total detected glycan pool. HMW % and LMW % are reported as a percent of the total detected polypeptide molecular weight variants. Values are normalized to low ethanol. Ethanol was fed daily to increase bioreactor concentrations by 0.072% (Low Ethanol) and 0.144% (High Ethanol) v/v in a 14 day fed-batch process.

As shown in FIG. 10, high ethanol concentration was associated with less Man5 and G0 glycan species, greater G1F and G2F glycan species, and less high and low molecular weight species.

V. Addition of Ethanol Using Bench-Scale Bioreactors and Two Different Feed Formulations Materials and Methods:

Antibody production was performed as described above for mAb 1.

Ethanol was fed daily between 0.0% and 0.018% v/v. Calculated cumulative cell culture concentration (concentration in vessel at time of cell harvest) of ethanol ranged between 0.0%-0.2% v/v. Bioreactor physical conditions were maintained at a pH of 7.0±0.2 shifted to 6.8±0.1, dissolved oxygen maintained at 30% air saturation and a constant temperature of 35° C. Basal and feed media were fully synthetic and chemically defined containing no animal derived components.

The same basal media was used in formulation #1 and #2. Feed formulation #1 and #2 were similar in composition containing the same type and amount of amino acids and vitamins. Salt and metal ion type and concentration were slightly varied. Both feeds were fully synthetic and chemically defined containing no animal derived components.

Results

Figure 11:
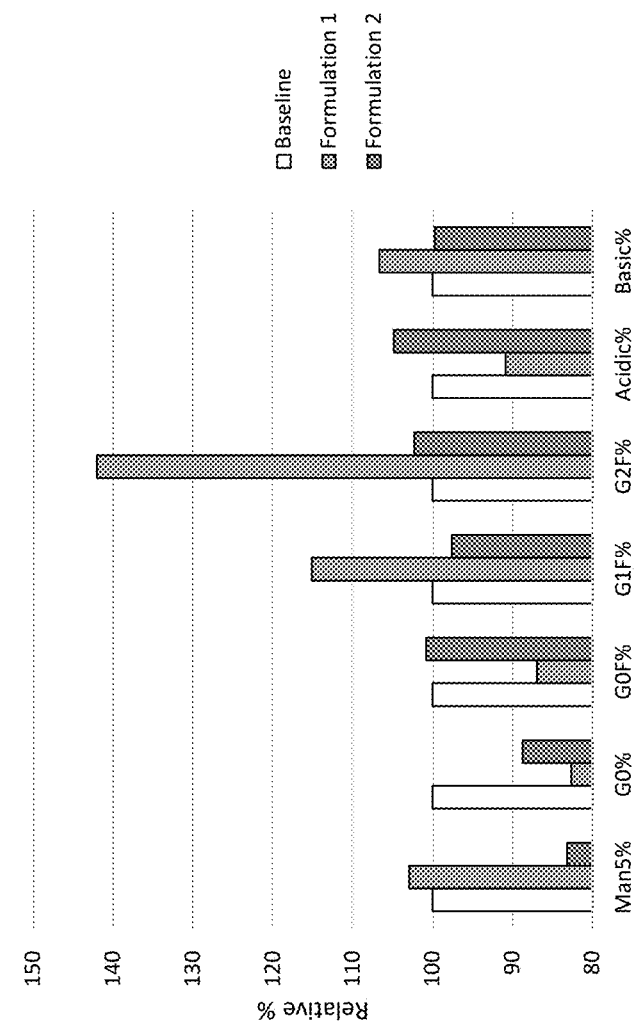
FIG. 11 depicts the impact on Man5%, G0%, G0F %, G1F %, G2F %, Acidic % and Basic % species using two different feed formulations. The same basal media was used in formulation 1 and 2. Formulation 1 and 2 feeds were very similar in composition, containing the same type and amount of amino acids and vitamins. Salt and metal ion type and concentration were slightly varied. Man5%, G0%, G0F %, G1F % and G2F % glycan species are reported as a percent of the total detected glycan pool. Acidic % and Basic % are reported as a percent of the total detected polypeptide charge species variants. Values are normalized to Baseline lacking ethanol. Ethanol was fed daily to increase bioreactor concentrations by 0.0% (Baseline) and 0.018% (Formulation 1 and Formulation 2) v/v in a 14 day fed-batch process.

As shown in FIG. 11, ethanol supplementation into Formulation 1 resulted in increased Man5, G1F, and G2F glycan species as well as basic charge variants. In contrast, this combination resulted in less G0 and G0F glycan species as well as less acidic charge variants. Ethanol supplementation of Formulation 2 resulted in decreased Man5, G0, and G1F glycan species but greater G0F and G2F glycan species as well as higher amounts of acidic charge variants (FIG. 11).

III. Addition of Ethanol Using Microscale Bioreactors for Production of a Different Monoclonal Antibody Materials and Methods:

Antibody production was performed as described above for mAb 2. This cell line is a CHO.DG44 derived clone producing mAb 2.

Ethanol was fed daily between 0.0% and 0.15% v/v. Calculated cumulative cell culture concentration (concentration in vessel at time of cell harvest) of ethanol ranged between 0.0%-1.35% v/v. Bioreactor physical conditions were maintained at a pH of 7.0±0.1 shifted to 6.8±0.1, dissolved oxygen maintained at 30% air saturation and a constant temperature of 35° C. Basal and feed media were fully synthetic and chemically defined containing no animal derived components.

Results

Figure 12:
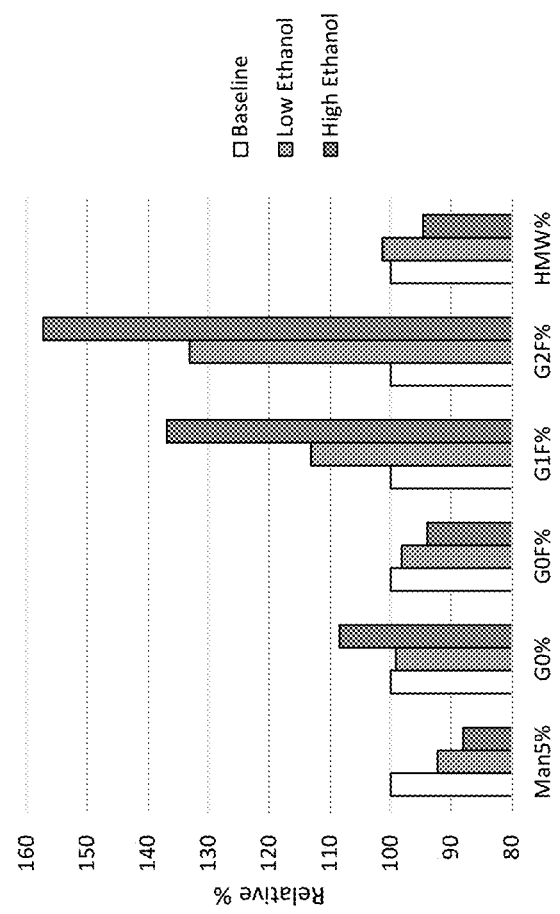
FIG. 12 depicts the impact on Man5%, G0%, G0F %, G1F %, G2F % and HMW % using microscale bioreactors and a CHO.DG44 cell line to produce mAb 2. Man5%, G0%, G0F %, G1F % and G2F % glycan species are reported as a percent of the total detected glycan pool. HMW % is reported as a percent of the total detected polypeptide molecular weight variants. Values are normalized to Baseline. Ethanol was fed daily to increase bioreactor concentrations by 0.0% (Baseline), 0.05% (Low Ethanol) and 0.15% (High Ethanol) v/v in a 13 day fed-batch process.

As shown in FIG. 12, higher ethanol concentrations are associated with decreased Man5 and G0F glycan species, increased G0, G1F, and G2F glycan species, and decreased high molecular weight species.

Ethanol supplementation altered glycosylation profile, antibody aggregates and acidic and basic charge variants. These effects sometimes varied among varying cell lines, mAb products and/or feed formulations.

In most cases ethanol decreased Man5%, G0% and G0F % and increased the mature glycan species G1F % and G2F %.

Example 3: Addition of Fatty Acids to Cell Culture Medium Improves Production of Recombinant Polypeptides Exogenous fatty acid supplementation could potentially decrease intracellular energy consumption since adenosine triphosphate (ATP) is consumed in the conversion of acetyl-CoA to malonyl-CoA, the primary building block of intracellular fatty acids. Furthermore, fatty acid supplementation possibly strengthens membrane integrity as the majority of cellular membranes are composed of C16 and C18 length phospholipids.

I. Determination of Cytotoxicity

Fatty acid cytotoxicity to CHO.DXB11 cells was determined by daily feed dosing. 4 mL of CHO cells at 4 $e^6$/mL cellular density were seeded into 6 well deep plates, mixed at 150 RPM, and daily fed fatty acids. Fatty acids were solubilized in ethanol and fed once daily to increase well plate concentration from 10 µM to 160 µM. Cell growth rate and cell viability were negatively affected at varying levels—dependent on the individual fatty acid. Oleic acid, linoleic acid and linolenic acid became toxic around 40 µM daily feeding concentration. Myristic acid, palmitic acid and stearic acid became toxic around 80 M daily feeding concentration. Cholesterol started to become toxic around 50 µM daily feeding concentration.

II. Addition of Oleic Acid Using Bench-Scale Bioreactors

Materials and Methods:

Antibody production was performed as described above for mAb 1.

Feed media was supplemented with fatty acids to determine if fatty acids altered mAb properties. Feed media was fed daily in a fed-batch process using bench-scale (2 L working volume) bioreactors. Oleic acid was fed daily to increase working bioreactor concentration by 40 M. Calculated cumulative cell culture concentration (concentration in vessel at time of cell harvest) of oleic acid was 440 µM. The media used for baseline measurements did not contain any fatty acids or ethanol.

Bioreactor physical conditions were maintained at a pH of 7.0±0.2, dissolved oxygen at 30% air saturation, temperature of 35° C. during logarithmic cellular growth phase and shifted to 29° C. during cellular production phase (temperature was shifted one day before max viable cell density was reached). Basal and feed media were fully synthetic and chemically defined containing no animal derived components.

Figure 13:
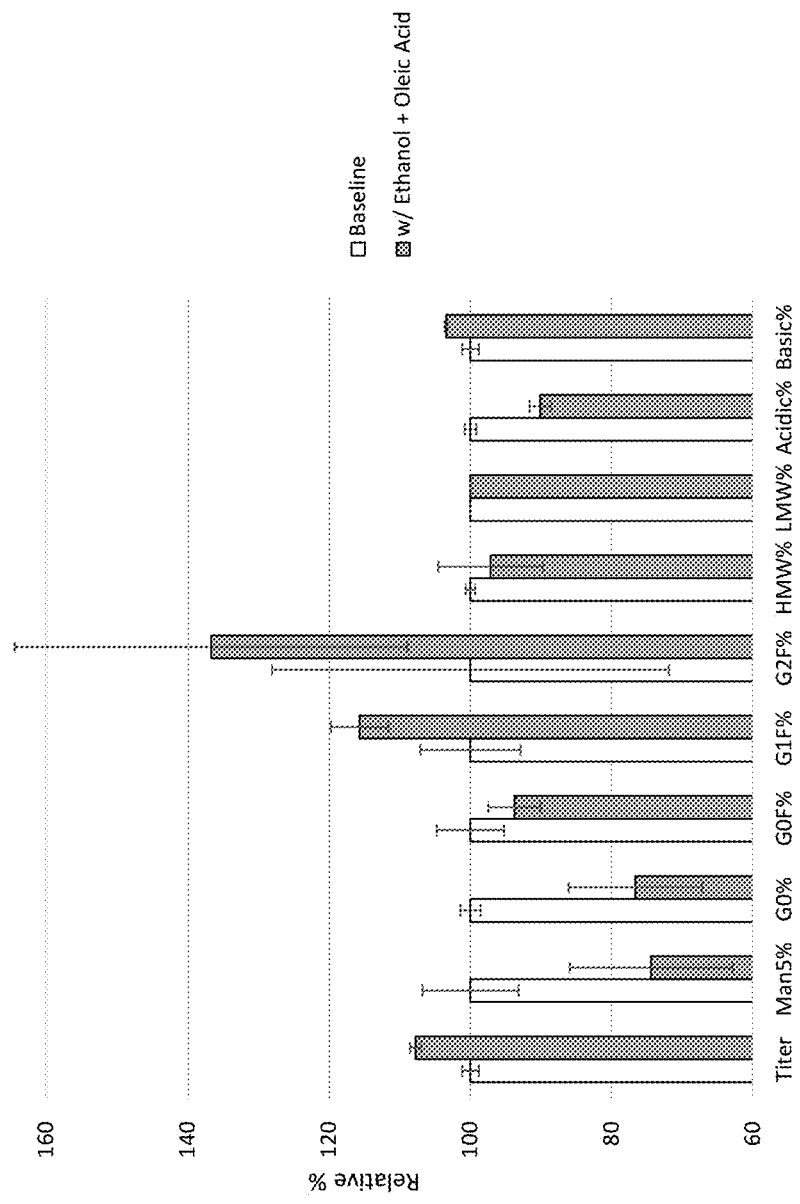
FIG. 13 depicts the synergistic impact on Titer, Man5%, G0%, G0F %, G1F %, G2F %, HMW %, LMW %, Acidic % and Basic % using bench-scale bioreactors supplemented with both ethanol and oleic acid. Titer is reported as volumetric titer. Man5%, G0%, G0F %, G1F % and G2F % glycan species are reported as a percent of the total detected glycan pool. HMW % and LMW % are reported as a percent of the total detected polypeptide molecular weight variants. Acidic % and Basic % are reported as a percent of the total detected polypeptide charge species variants. Values are normalized to Baseline, which contains no ethanol or oleic acid. Ethanol was fed daily to increase bioreactor concentrations by 0.0% (Baseline) and 0.057% (w/Ethanol+Oleic Acid) v/v and oleic acid was fed daily to increase bioreactor concentrations by 0 M (Baseline) and 40 µM (w/Ethanol+Oleic Acid) in a 14 day fed-batch process.

Results:

As shown in FIG. 13, addition of oleic acid to media increased monoclonal antibody titer, decreased Man5, G0, and G0F glycan species, increased G1F and G2F glycan species, decreased high molecular weight species, and decreased acidic charge variants.

III. Addition of Oleic Acid Using Bench-Scale Bioreactors Using Bench-Scale Bioreactors with Different Physical and Feed Conditions Materials and Methods:

Antibody production was performed as described above for mAb 1.

Ethanol supplemented media was further supplemented with fatty acids to determine if fatty acids altered mAb properties. Feed media was fed daily in a fed-batch process using bench-scale (2 L working volume) bioreactors. Oleic acid was fed daily to increase working bioreactor concentration by 40 µM. Calculated cumulative cell culture concentration (concentration in vessel at time of cell harvest) of oleic acid was 440 µM. Media used for baseline measurements contains ethanol but no fatty acids.

Bioreactor physical conditions were maintained at a pH of 7.0±0.2, dissolved oxygen at 30% air saturation, temperature of 35° C. during logarithmic cellular growth phase and shifted to 31° C. during cellular production phase (temperature was shifted one day before max viable cell density was reached). Basal and feed media are fully synthetic and chemically defined containing no animal derived components.

Figure 14:
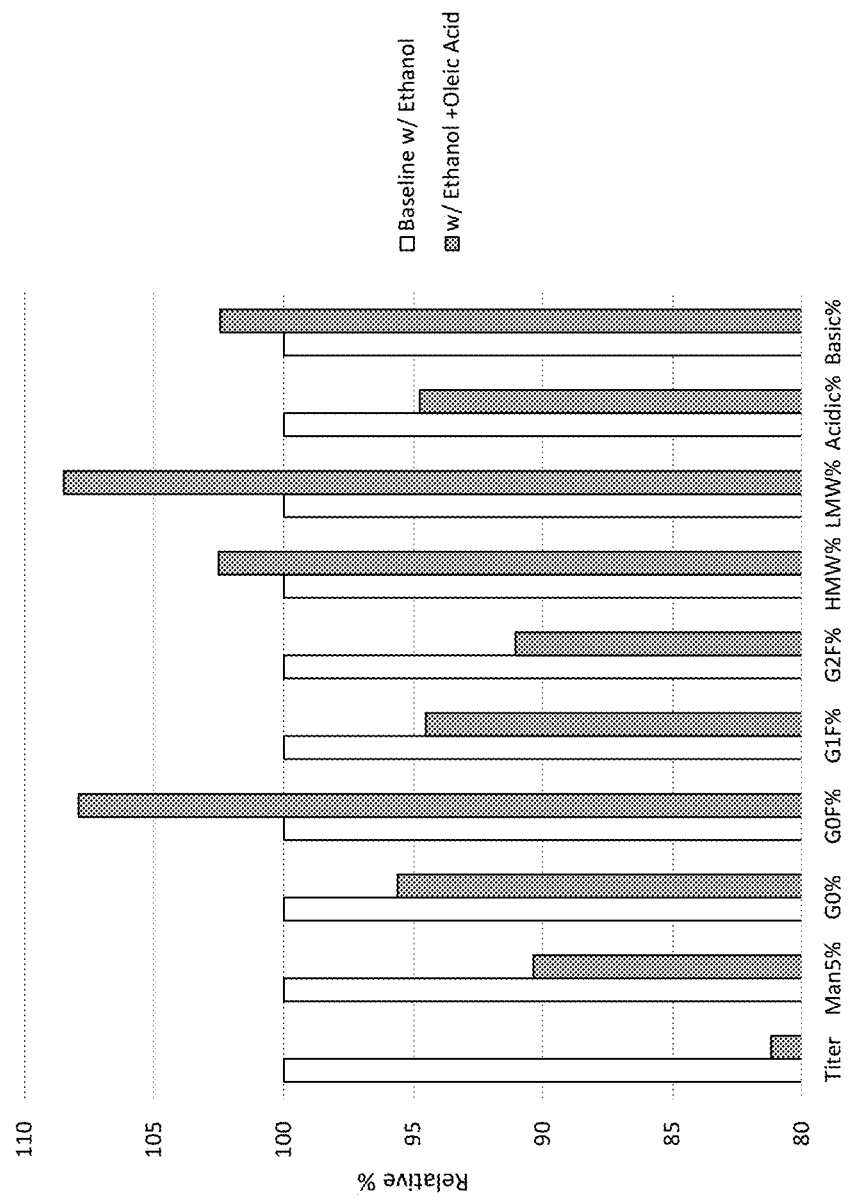
FIG. 14 depicts the impact on Titer, Man5%, G0%, G0F %, G1F %, G2F %, HMW %, LMW %, Acidic % and Basic % using bench-scale bioreactors. Titer is reported as volumetric titer. Man5%, G0%, G0F %, G1F % and G2F % glycan species are reported as a percent of the total detected glycan pool. HMW % and LMW % are reported as a percent of the total detected polypeptide molecular weight variants. Acidic % and Basic % are reported as a percent of the total detected polypeptide charge species variants. Values are normalized to Baseline w/Ethanol. Oleic acid was fed daily to increase bioreactor concentrations by 0 M (Baseline w/Ethanol) and 40 µM (w/Ethanol+Oleic Acid) in a 14 day fed-batch process.

Results:

As shown in FIG. 14, addition of oleic acid resulted in decreased antibody titer, decreased Man5, G0, G1F, and G2F glycan species, increased G0F glycan species, increased high and low molecular weight species, decreased acidic charge variants, and increased basic charge variants. Oleic acid supplementation appeared to further reduce Man5% levels from that of just ethanol supplementation. It additionally altered fucosylated glycan species and reduced acidic charge variants.

Overall, oleic acid dissolved in ethanol was observed to increase G0F % glycan profile. Supplementation appeared to reduce Man5%, G0%, G1F %, G2F % glycan profile in addition to reducing acidic charge species.

Example 4: Addition of Sodium Chloride to Medium for Comparison to Addition of Lithium Chloride Sodium concentration in a normal cellular interstitial environment is typically 136-145 mM and chloride is typically 96-106 mM. For the lithium supplemented medium described above, approximately 1 mM lithium chloride is added daily, which is roughly a 1% increase in chloride ion concentration. Accordingly, this Example shows that the improvement in cell productivity results from increased lithium ion concentration rather than increased amounts of chloride ion.

Materials and Methods:

Monoclonal antibody 3 (mAb3) is a monoclonal antibody produced using recombinant DNA technology. The expression vector is fully synthetic with both heavy- and light-chain gene sequences regulated by strong constitutive promoters. Gene sequences were confirmed by DNA sequencing. The expression vector was linearized by restriction enzymes and stably transfected into CHO.DXB11 cells by electroporation. Gene amplification steps were performed with increasing concentrations of methotrexate. Single cell cloning was performed after gene amplification. Select single cell clones were expanded and cryopreserved. The cell line used was a CHO.DXB11 derived clone.

Sodium chloride was fed daily at 4.59 mM and 9.18 mM using two different process strategies. Process strategy 1 was maintained at 36.5° C. then shifted to 31° C. during production phase. Process strategy 2 was maintained at 36.5° C. then shifted to 31° C. during production phase then re-shifted back to 36.5° C. during late production phase. Both process strategies were maintained at 30% air saturation and a pH of 7.0±0.2. Other glycan species and HMW % and LMW % are not listed because no significant change in levels were observed from sodium chloride supplementation.

Figure 15A:
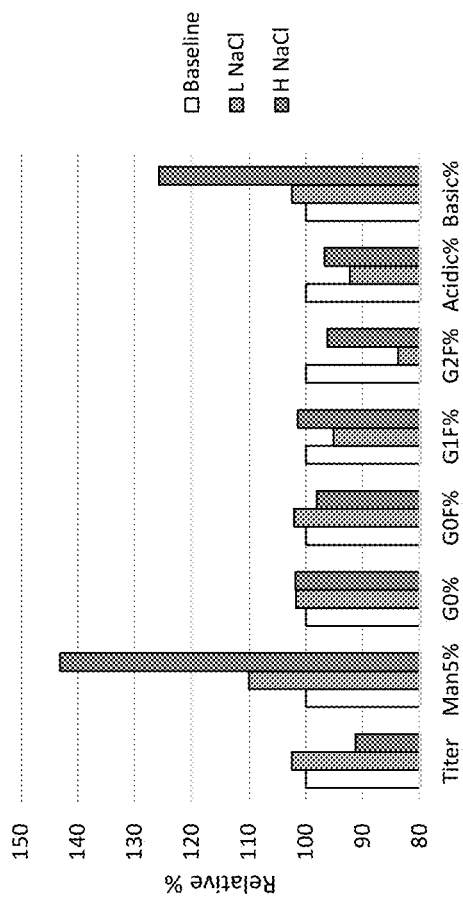
FIG. 15A depicts the impact of spiking cell culture medium with sodium chloride on Titer, Man5%, G0%, G0F %, G1F, G2F %, Acidic % and Basic % species using microscale bioreactors. Process strategy 1 involved a single temperature shift strategy. Titer is reported as volumetric titer. Man5%, G0%, G0F %, G1F % and G2F % glycan species are reported as a percent of the total detected glycan pool. Acidic % and Basic % are reported as a percent of the total detected polypeptide charge species variants. Values are normalized to baseline. Sodium chloride was fed daily to increase bioreactor concentrations by 4.59 mM (L NaCl) and 9.18 mM (H NaCl) in a 12 day fed-batch process.
Figure 15B:
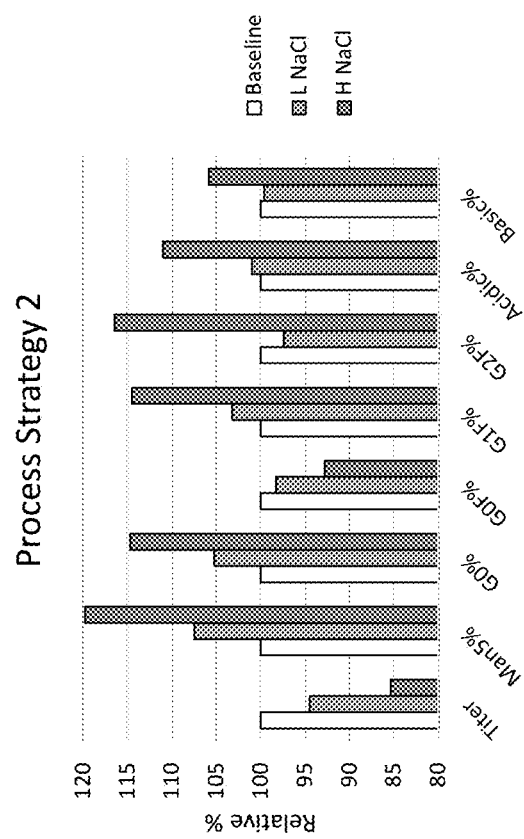
FIG. 15B depicts the impact of spiking cell culture medium with sodium chloride on Titer, Man5%, G0%, G0F %, G1F, G2F %, Acidic % and Basic % species using microscale bioreactors. Process strategy 2 involved a dual temperature shift strategy. Titer is reported as volumetric titer. Man5%, G0%, G0F %, G1F % and G2F % glycan species are reported as a percent of the total detected glycan pool. Acidic % and Basic % are reported as a percent of the total detected polypeptide charge species variants. Values are normalized to baseline. Sodium chloride was fed daily to increase bioreactor concentrations by 4.59 mM (L NaCl) and 9.18 mM (H NaCl) in a 12 day fed-batch process.

Results:

As shown in FIG. 15A and FIG. 15B, addition of sodium chloride to media decreased monoclonal antibody titer and G0F glycan species. Man5, G0, G1F and G2F glycan species increased with acidic and basic charge variants.

When supplementing increased levels of sodium chloride, mAb properties were altered and significantly different than when supplemented with lithium chloride. Sodium chloride reduced titer levels, altered glycosylation profile differently, increased basic % and did not change LMW % or HMW %. The data indicate that the effects observed with lithium chloride are due to the lithium ion and not chloride.

Example 5: Supplementation of Media with Fatty Acids, Methyl Esters, Sterols, Glycerides and Isoprenoids A variety of fatty acids, methyl esters, sterols, glycerides and isoprenoids were added to cell culture media used to produce two separate monoclonal antibodies followed by evaluation of titer and product quality.

Materials and Methods:

Monoclonal antibodies 1 (mAb1) and 4 (mAb4) were produced using two separate cell lines according to methods described in the previous Examples. Titer, percent of high molecular weight and low molecular weight species, acidic and basic charge variants, and glycosylation species profiles were assessed as in the previous Examples.

Figure 18A:
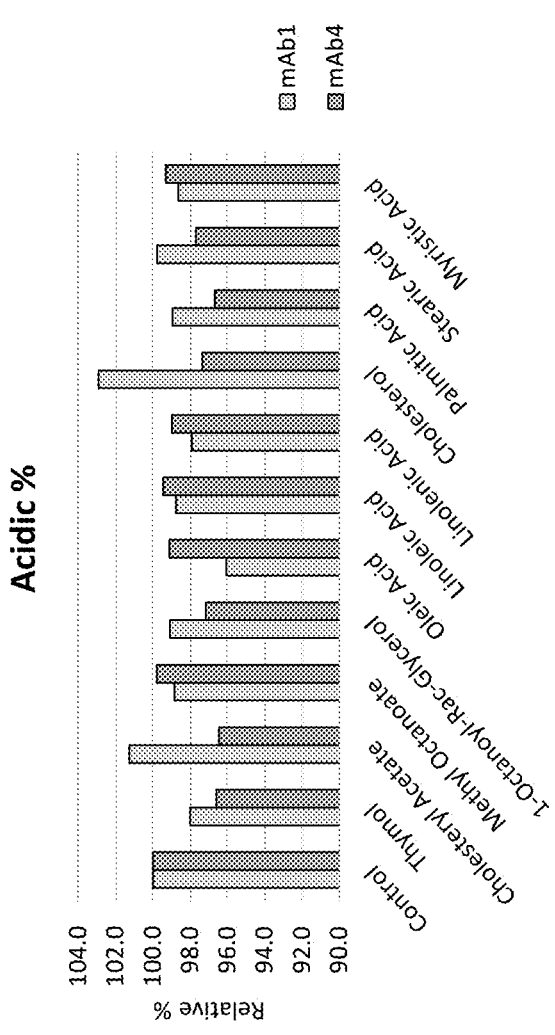
FIG. 18A depicts the impact of addition of various types of fatty acids to the culture medium with respect to acidic charge species for two separate monoclonal antibodies (mAb1 and mAb4) produced by two separate cell lines. Acidic % is reported as a percent of the total detected polypeptide charge species variants. Values are normalized to control.
Figure 18B:
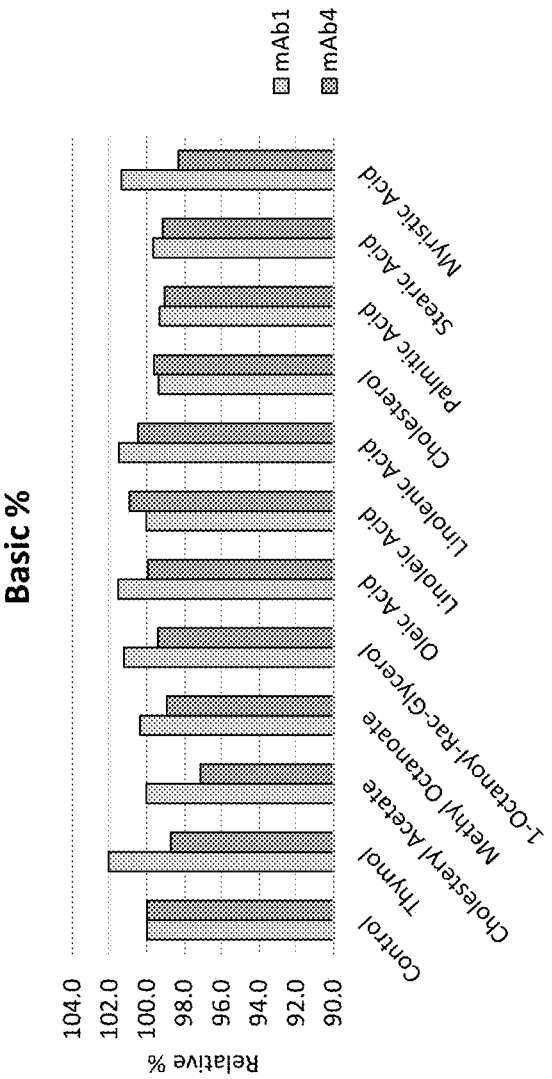
FIG. 18B depicts the impact of addition of various types of fatty acids to the culture medium with respect to basic charge species for two separate monoclonal antibodies (mAb1 and mAb4) produced by two separate cell lines. Basic % is reported as a percent of the total detected polypeptide charge species variants. Values are normalized to control.

Fatty acids were dissolved in ethanol and fed daily according to Table 5 using two different process strategies for mAb1 and mAb4. The mAb1 process strategy was maintained at 37° C. then shifted to 31° C. during late exponential phase, with the pH being maintained at 7.0±0.2 throughout the culture. The mAb4 process strategy was maintained at 36.5° C. then shifted to 33° C. during production phase, with the pH being shifted from 7.0±0.1 to 6.8±0.1 in the late exponential phase. Both process strategies were maintained at 30% air saturation (FIG. 18A). Media supplementation with cholesterol, palmitic acid, and stearic acid decreased basic charge variants for mAb1 production (FIG. 18B) while thymol, cholesteryl acetate, methyl octanoate, 1-octanoyl-rac-glycerol, cholesterol, palmitic acid, stearic acid, and myristic acid decreased the relative percentage of basic charge variants for mAb4 (FIG. 18B).

Figure 19A:
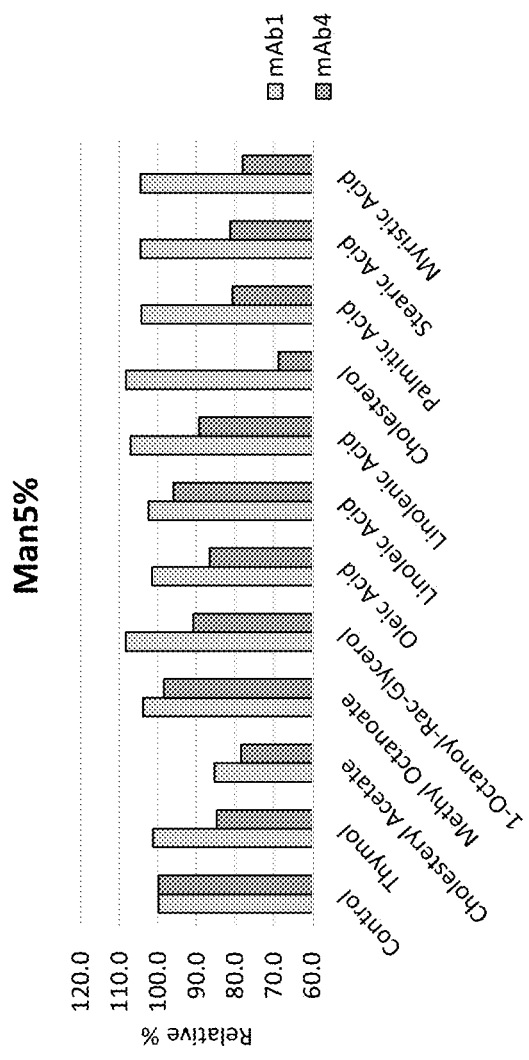
FIG. 19A depicts the impact of addition of various types of fatty acids to the culture medium with respect to Man5% glycan species for two separate monoclonal antibodies (mAb1 and mAb4) produced by two separate cell lines. Man5% glycan species is reported as a percent of the total detected glycan pool. Values are normalized to control.
Figure 19B:
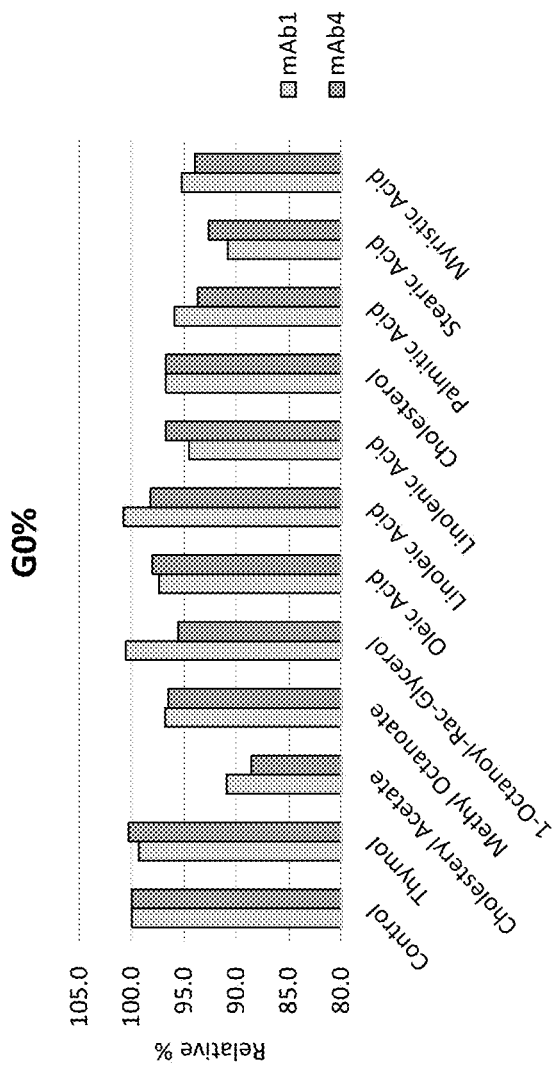
FIG. 19B depicts the impact of addition of various types of fatty acids to the culture medium with respect to G0% glycan species for two separate monoclonal antibodies (mAb1 and mAb4) produced by two separate cell lines. G0% glycan species is reported as a percent of the total detected glycan pool. Values are normalized to control.

Decreased Man5 glycan species were observed following media supplementation with cholesteryl acetate for mAb1 production (FIG. 19A) while supplementation with thymol, cholesteryl acetate, methyl octanoate, 1-octanoyl-rac-glycerol, oleic acid, linoleic acid, linolenic acid, cholesterol, palmitic acid, stearic acid, and myristic acid decreased the relative percentage of Man5 glycan species for mAb4 production (FIG. 19A). Decreased G0 glycan species for mAb1 were observed following media supplementation with thymol, cholesteryl acetate, methyl octanoate, oleic acid, linolenic acid, cholesterol, palmitic acid, stearic acid, and myristic acid (FIG. 19B) whereas supplementation with cholesteryl acetate, methyl octanoate, 1-octanoyl-rac-glycerol, oleic acid, linoleic acid, linolenic acid, cholesterol, palmitic acid, stearic acid, and myristic acid decreased the relative percentage of G0 glycan species for mAb4 production (FIG. 19B). Finally, decreased G0F glycan species were observed for mAb1 following media supplementation with

TABLE 5

Feed conditions used for cell culture.

| Supplement | mAb1 Feed Conditions | | mAb4 Feed Conditions | |
| --- | --- | --- | --- | --- |
| | Daily Fatty Acid Feed (µM) | Daily Ethanol Feed (% v/v) | Daily Fatty Acid Feed (µM) | Daily Ethanol Feed (% v/v) |
| Control | 0.0 | 0.05 | 0.0 | 0.09 |
| Thymol | 2.7 | 0.05 | 5.0 | 0.09 |
| Cholesteryl acetate | 10.7 | 0.05 | 20.0 | 0.09 |
| Methyl octanoate | 2.7 | 0.05 | 5.0 | 0.09 |
| 1-Octanoyl-rac-glycerol | 2.7 | 0.05 | 5.0 | 0.09 |
| Oleic Acid | 10.7 | 0.05 | 20.0 | 0.09 |
| Linoleic acid | 10.7 | 0.05 | 20.0 | 0.09 |
| Linolenic acid | 10.7 | 0.05 | 20.0 | 0.09 |
| Cholesterol | 7.4 | 0.05 | 20.0 | 0.09 |
| Palmitic Acid | 10.7 | 0.05 | 20.0 | 0.09 |
| Stearic acid | 10.7 | 0.05 | 20.0 | 0.09 |
| Myristic acid | 10.7 | 0.05 | 20.0 | 0.09 |

Results

Figure 16:
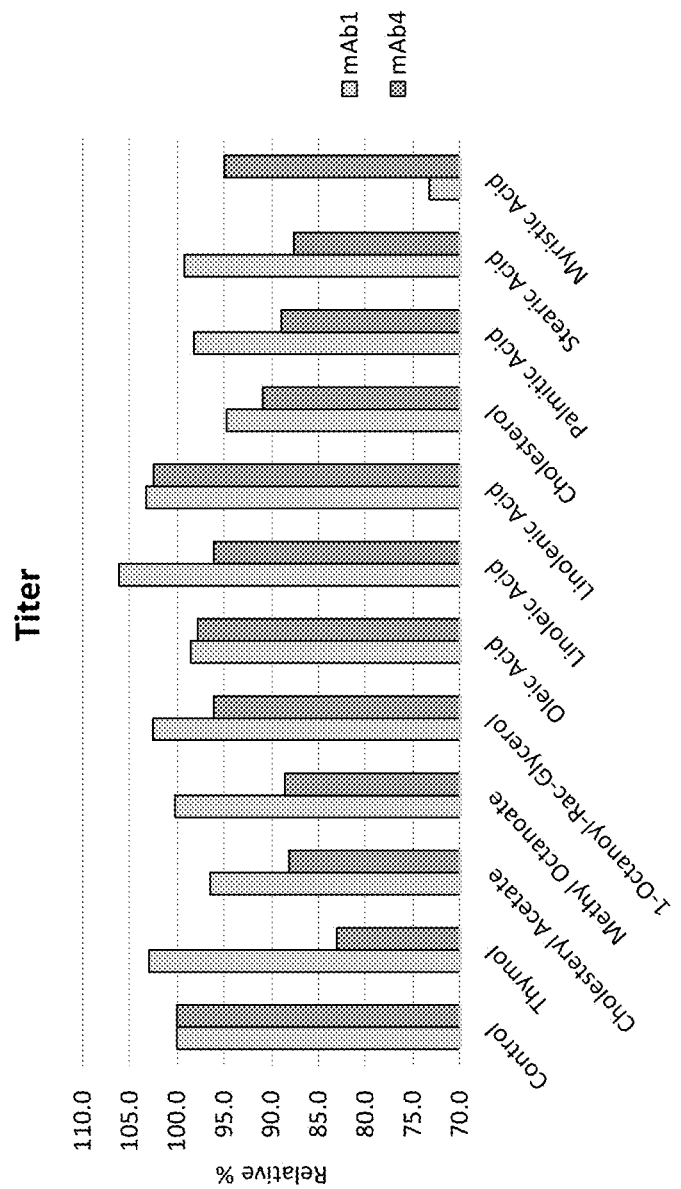
FIG. 16 depicts the impact of addition of various types of fatty acids to the culture medium with respect to titer for two separate monoclonal antibodies (mAb1 and mAb4) produced by two separate cell lines. Titer is reported as volumetric titer. Values are normalized to control.
Figure 17A:
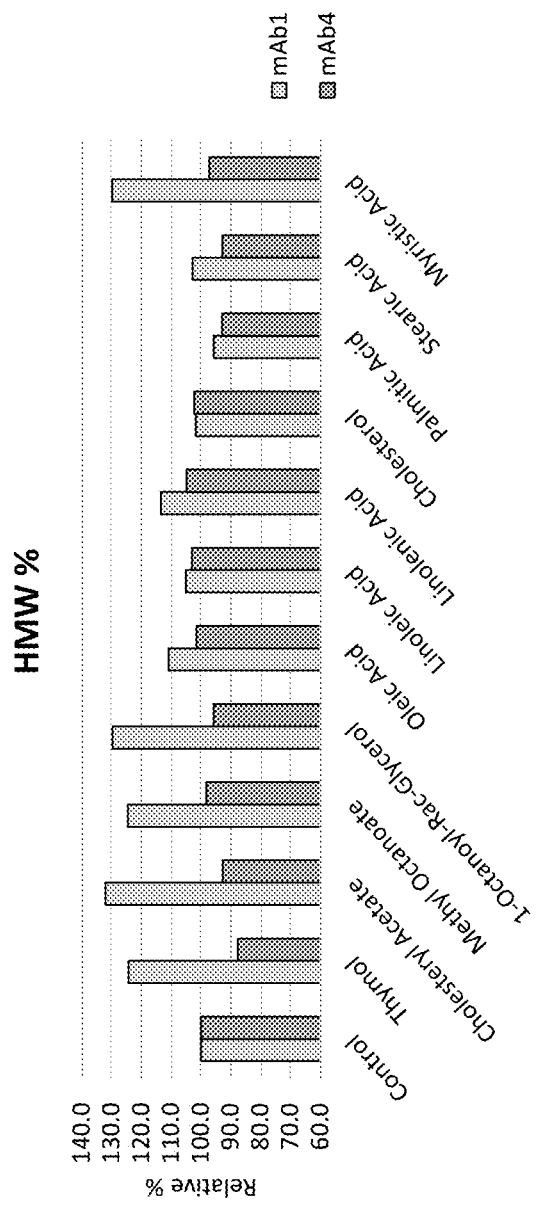
FIG. 17A depicts the impact of addition of various types of fatty acids to the culture medium with respect to high molecular weight (HMW) species for two separate monoclonal antibodies (mAb1 and mAb4) produced by two separate cell lines. HMW % is reported as a percent of the total detected polypeptide molecular weight variants. Values are normalized to control.
Figure 17B:
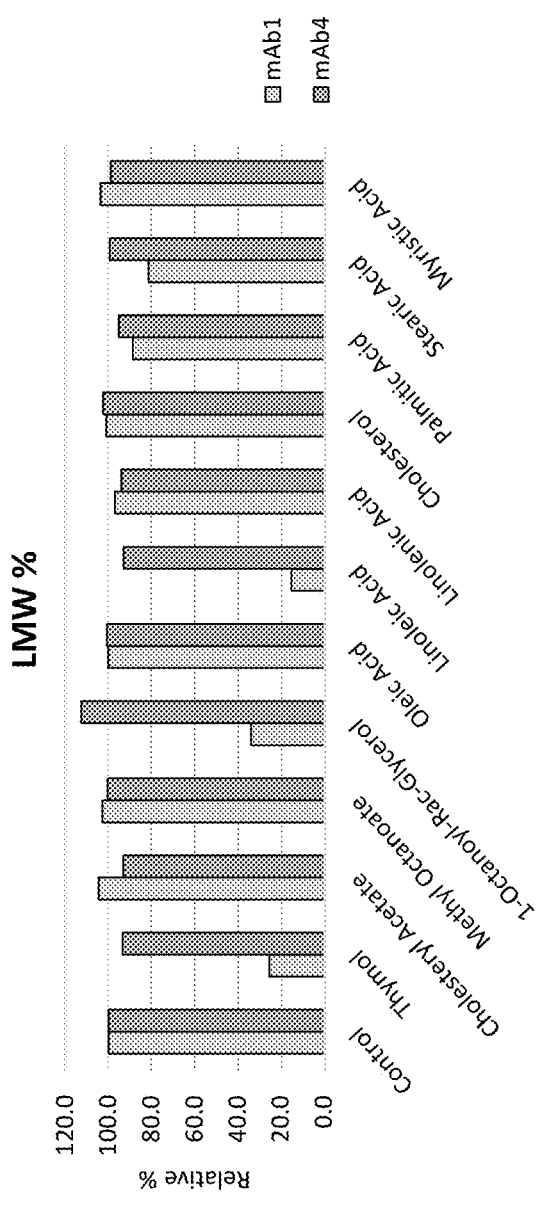
FIG. 17B depicts the impact of addition of various types of fatty acids to the culture medium with respect to low molecular weight (LMW) species for two separate monoclonal antibodies (mAb1 and mAb4) produced by two separate cell lines. LMW % is reported as a percent of the total detected polypeptide molecular weight variants. Values are normalized to control.

As shown in FIG. 16, media supplementation with thymol, 1-octanoyl-Rac-glycerol, linoleic acid, and linolenic acid increased the titer of mAb1 while linolenic acid increased production of mAb4 With respect to HMW species, palmitic acid decreased the relative percentage versus controls for mAb1 (FIG. 17A) whereas thymol, cholesterol acetate, methyl octanoate, 1-octanoyl-rac-glycerol, palmitic acid, stearic acid, and myristic acid decreased the relative percentage of HMW species for mAb4 (FIG. 17A). Low molecular weight species were decreased for mAb1 using thymol, 1-octanoyl-rac-glycerol, linoleic acid, linolenic acid, palmitic acid, and stearic acid (FIG. 17B) whereas thymol, cholesteryl acetate, linoleic acid, and palmitic acid decreased LMW species for mAb4 (FIG. 17B).

Figure 20:
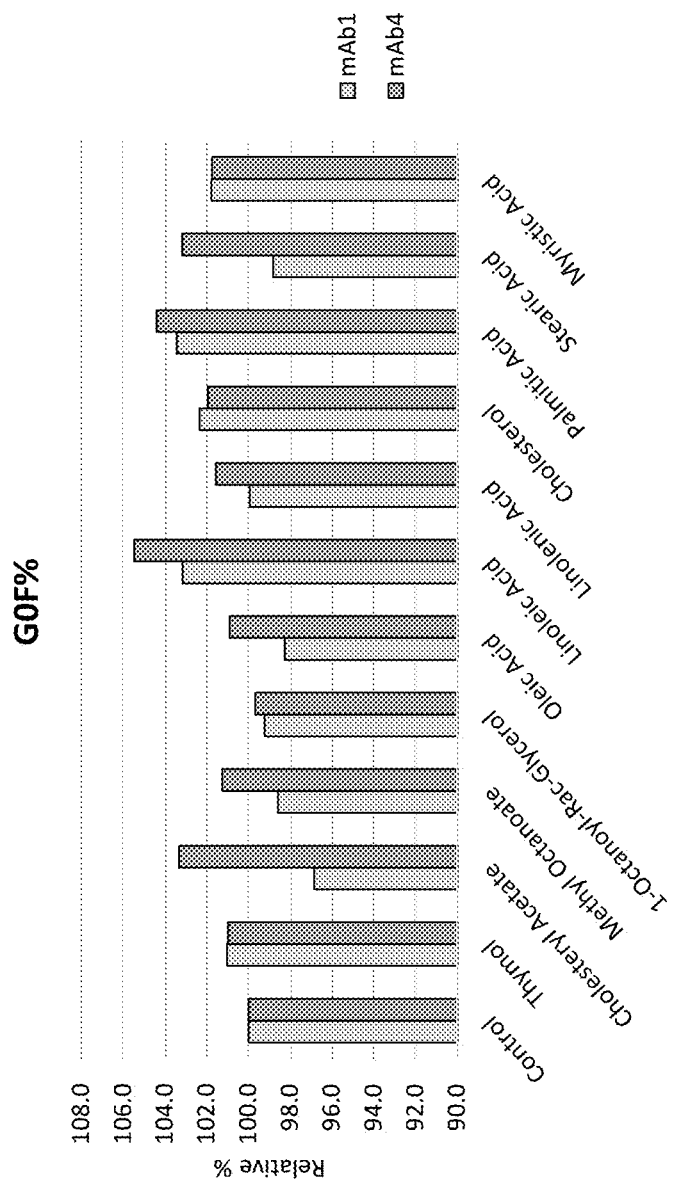
FIG. 20 depicts the impact of addition of various types of fatty acids to the culture medium with respect to G0F % glycan species for two separate monoclonal antibodies (mAb1 and mAb4) produced by two separate cell lines. G0F % glycan species is reported as a percent of the total detected glycan pool. Values are normalized to control.

Acidic charge variants were decreased for mAb1 production via supplementation with thymol, methyl octanoate, 1-octanoyl-rac-glycerol, oleic acid, linoleic acid, linolenic acid, palmitic acid, and myristic acid (FIG. 18A) whereas thymol, cholesteryl acetate, 1-octanoyl-rac-glycerol, oleic acid, linoleic acid, linolenic acid, palmitic acid, stearic acid, and myristic acid decreased acidic charge variants for mAb4 cholesteryl acetate, methyl octanoate, 1-octanoyl-rac-glycerol, oleic acid, and myristic acid (FIG. 20) whereas supplementation with 1-octanoyl-rac-glycerol decreased the relative percentage of G0F glycan species for mAb4 production (FIG. 20).

We claim:

1. A method for producing one or more recombinant polypeptides from an engineered mammalian cell, the method comprising:
    (a) culturing said engineered mammalian cell in a medium under suitable conditions for the production of said one or more recombinant polypeptides, and increasing the concentration of lithium ions in the medium during the culturing; and
    (b) producing said one or more recombinant polypeptides, wherein the medium comprises
        (i) a basal medium or a feed medium; and
        (ii) one or more sources of lithium ions.

2. The method of claim 1, wherein the method further comprises (c) isolating said one or more recombinant polypeptides.

3. The method of claim 1, wherein the medium is (a) a basal medium; or (b) a feed medium.

4. The method of claim 1 wherein said one or more recombinant polypeptides is an antibody or fragment thereof.

5. The method of claim 4, wherein said antibody is a monoclonal antibody.

6. The method of claim 5, wherein the monoclonal antibody inhibits the growth of a proliferating cell.

7. The method of claim 4, wherein said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), integrin $\alpha_v\beta_3$, neural apoptosis-regulated proteinase 1, integrin $\alpha_{11b}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7.

8. The method of claim 5, wherein said monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

9. A method for modulating the glycosylation profile of one or more recombinant polypeptides produced by a genetically engineered mammalian cell, the method comprising:
(a) culturing said mammalian cell in a medium under suitable conditions for the production of said one or more recombinant polypeptides, and increasing the concentration of lithium ions in the medium during the culturing; and
(b) producing said one or more recombinant polypeptides, wherein the medium comprises
(i) a basal medium or a feed medium; and
(ii) one or more sources of lithium ions,
and wherein said one or more recombinant polypeptides has a modulated glycosylation profile compared to recombinant polypeptides produced by mammalian cells that are not cultured in the medium.

10. The method of claim 9, wherein said modulated glycosylation profile comprises modulated terminal mannose glycan species.

11. The method of claim 9, wherein said modulated glycosylation comprises modulation of one or more glycan species selected from mannose-5-N-acetylglycosamine-2 (Man5), mannose-6-N-acetylglycosamine-2 (Man6), mannose-3-N-acetylglucosamine-4 (G0), mannose-3-N-acetylglucosamine-4-fucose (G0F), mannose-3-N-acetylglucosamine-4-galactose-1-fucose (G1F), and/or mannose-3-N-acetylglucosamine-4-galactose-2-fucose (G2F).

12. The method of claim 9, wherein the ratio of the terminal mannose glycan species to the total sum of glycan species is modulated by about 40% to about 50%.

13. The method of claim 9, wherein said one or more recombinant polypeptides is an antibody or fragment thereof.

14. The method of claim 13, wherein said antibody is a monoclonal antibody.

15. The method of claim 14, wherein the monoclonal antibody inhibits the growth of a proliferating cell.

16. The method of claim 13, wherein said antibody or fragment thereof binds to HER2, TNF-α, VEGF-A, α4-integrin, CD20, CD52, CD25, CD11a, EGFR, respiratory syncytial virus (RSV), glycoprotein IIb/IIIa, IgG1, IgE, complement component 5 (C5), B-cell activating factor (BAFF), CD19, CD30, interleukin-1 beta (IL1β), prostate specific membrane antigen (PSMA), CD38, RANKL, GD2, SLAMF7 (CD319), proprotein convertase subtilisin/kexin type 9 (PCSK9), dabigatran, cytotoxic T-lymphocyte-associated protein 4 (CTLA4), interleukin-5 (IL-5), programmed cell death protein (PD-1), VEGFR2 (KDR), protective antigen (PA) of *B. anthracis*, interleukin-17 (IL-17), interleukin-6 (IL-6), interleukin-6 receptor (IL6R), interleukin-12 (IL-12), interleukin 23 (IL-23), sclerostin (SOST), myostatin (GDF-8), activin receptor-like kinase 1, delta like ligand 4 (DLL4), angiopoietin 3, VEGFR1, selectin, oxidized low-density lipoprotein (oxLDL), platelet-derived growth factor receptor beta, neuropilin 1, Von Willebrand factor (vWF), integrin $\alpha_v\beta_3$, neural apoptosis-regulated proteinase 1, integrin $\alpha_{11b}\beta_3$, beta-amyloid, reticulon 4 (RTN4)/Neurite Outgrowth Inhibitor (NOGO-A), nerve growth factor (NGF), LINGO-1, myelin-associated glycoprotein, or integrin α4β7.

17. The method of claim 14, wherein said monoclonal antibody is trastuzumab, pertuzumab, infliximab, adalimumab, bevacizumab, ranibizumab, natalizumab, rituximab, alemtuzumab, daclizumab, efalizumab, golimumab, certolizumab, cetuximab, panitumumab, palivizumab, abciximab, basiliximab, ibritumomab, omalizumab, eculizumab, abciximab, alirocumab, basiliximab, belimumab, blinatumomab, brentuximab, canakinumab, capromab, daratumumab, denosumab, dinutuximab, eculizumab, elotuzumab, evolocumab, idarucizumab, ipilimumab, mepolizumab, necitumumab, nivolumab, obinutuzumab, ofatumumab, palivizumab, pembrolizumab, ramucirumab, raxibacumab, ecukinumab, siltuximab, tocilizumab, ustekinumab, alacizumab, denosumab, blosozumab, romosozumab, stamulumab, alirocumab, ascrinvacumab, enoticumab, evinacumab, evolocumab, icrucumab, inclacumab, nesvacumab, orticumab, ramucirumab, rinucumab, vesencumab, bococizumab, caplacizumab, demcizumab, etaracizumab, idarucizumab, ralpancizumab, tadocizumab, aducanumab, atinumab, fasinumab, fulranumab, gantenerumab, opicinumab, bapineuzumab, crenezumab, ozanezumab, ponezumab, refanezumab, solanezumab, tanezumab, and vedolizumab.

18. The method of claim 1, wherein the medium further comprises (c) ethanol; and/or (d) one or more fatty acids.

19. The method of claim 18, wherein said one or more fatty acids is selected from the group consisting of oleic acid, linoleic acid, linolenic acid, myristic acid, palmitic acid stearic acid, thymol, cholesteryl acetate, methyl octanoate, 1-octanoyl-rac-glycerol, cholesterol, butyric (C4), valeric (C5), caproic (C6), enanthic (C7), caprylic (C8), pelargonic (C9), capric (C10), undecylic (C11), lauric (C12), tridecylic (C13), myristic (C14), pentadecanoic (C15), margaric (C17), nonadecylic (C19), arachidic (C20), heneicosylic (C21), behenic (C22), tricosylic (C23), lignoceric (C24), pentacosylic (C25), cerotic (C26), heptacosylic (C27), montanic (C28), nonacosylic (C29), melissic (C30), hentriacontylic (C31), lacceroic (C32), psyllic (C33), geddic (C34), ceroplastic (C35), hexatriacontylic (C36), heptatriacontanoic (C37), and octatriacontanoic (C38) acids.

20. The method of claim 1, wherein said one or more sources of lithium ions is selected from the group of one or more of lithium acetate, lithium chloride, lithium carbonate, lithium oxybutyrate, lithium orotate, lithium bromide, lithium citrate, lithium fluoride, lithium iodide, lithium nitrate, and lithium sulfate.

21. The method of claim 1, wherein said lithium ions are present in a concentration from about 0.1 μM to about 25 mM.

22. The method of claim 1, wherein the concentration of lithium ions in the medium is increased daily by about 0.1 mM to about 1.11 mM.

23. The method of claim 22, wherein the concentration of lithium ions in the medium is increased daily by about 0.1 mM, about 0.11 mM, about 0.5 mM, about 0.44 mM, about 1 mM, or about 1.11 mM.

24. The method of claim 9, wherein the concentration of lithium ions in the medium is increased daily by about 0.1 mM to about 1.11 mM.

25. The method of claim 24, wherein the concentration of lithium ions in the medium is increased daily by about 0.1 mM, about 0.11 mM, about 0.5 mM, about 0.44 mM, about 1 mM, or about 1.11 mM.

* * * * *